US011369691B2

(12) United States Patent
Von Der Mülbe et al.

(10) Patent No.: US 11,369,691 B2
(45) Date of Patent: Jun. 28, 2022

(54) PHARMACEUTICAL COMPOSITION CONTAINING A STABILISED MRNA OPTIMISED FOR TRANSLATION IN ITS CODING REGIONS

(71) Applicant: CureVac AG, Tubingen (DE)

(72) Inventors: Florian Von Der Mülbe, Stuttgart (DE); Ingmar Hoerr, Tubingen (DE); Steve Pascolo, Tubingen (DE)

(73) Assignee: CureVac AG, Tübingen (DE)

( * ) Notice: Subject to any disclaimer, the term of this patent is extended or adjusted under 35 U.S.C. 154(b) by 826 days.

(21) Appl. No.: 15/005,986

(22) Filed: Jan. 25, 2016

(65) Prior Publication Data

US 2016/0136301 A1    May 19, 2016

Related U.S. Application Data

(60) Continuation of application No. 14/487,425, filed on Sep. 16, 2014, now Pat. No. 11,135,312, which is a
(Continued)

(30) Foreign Application Priority Data

Jun. 5, 2001   (DE) ............... 101 27 283.9

(51) Int. Cl.
*A61K 48/00*       (2006.01)
*C12N 15/67*       (2006.01)
(Continued)

(52) U.S. Cl.
CPC ........ *A61K 48/005* (2013.01); *A61K 38/1735* (2013.01); *A61K 38/1816* (2013.01); *A61K 38/19* (2013.01); *A61K 38/193* (2013.01); *A61K 38/28* (2013.01); *A61K 39/00* (2013.01); *A61K 39/0011* (2013.01); *A61K 39/00117* (2018.08); *A61K 39/001106* (2018.08); *A61K 39/001153* (2018.08); *A61K 39/001156* (2018.08); *A61K 39/001184* (2018.08); *A61K 39/001186* (2018.08); *A61K 39/001188* (2018.08); *A61K 39/001189* (2018.08); *A61K 39/001191* (2018.08); *A61K 39/001192* (2018.08); *A61K 39/001194* (2018.08); *A61K 39/001197* (2018.08); *A61K 39/0258* (2013.01); *A61K 39/12* (2013.01); *A61K 39/145* (2013.01); *A61K 39/21* (2013.01); *A61K 47/542* (2017.08); *A61K 47/6455* (2017.08); *A61K 48/0066* (2013.01); *A61K 48/0075* (2013.01); *A61K 48/0083* (2013.01); *C07K 14/005* (2013.01); *C07K 14/245* (2013.01); *C07K 14/4727* (2013.01); *C07K 14/4748* (2013.01); *C12N 7/00* (2013.01); *C12N 15/11* (2013.01); *C12N 15/67* (2013.01); *G16B 20/50* (2019.02); *A61K 48/00* (2013.01); *A61K 2039/53* (2013.01); *C12N 2310/334* (2013.01); *C12N 2310/336* (2013.01); *C12N 2740/16022* (2013.01); *C12N 2740/16034* (2013.01); *C12N 2760/14122* (2013.01); *C12N 2760/14134* (2013.01); *C12N 2760/16022* (2013.01); *C12N 2760/16034* (2013.01); *C12N 2760/16071* (2013.01); *C12N 2770/24122* (2013.01); *C12N 2770/24134* (2013.01);
(Continued)

(58) Field of Classification Search
CPC .............. A61K 2039/53; A61K 48/005; A61K 39/001189; A61K 39/001153; A61K 39/00117; A61K 39/001192; A61K 39/001106; A61K 39/001156; A61K 39/001186; A61K 39/001191; A61K 39/001194; A61K 39/001197; A61K 39/001188; A61K 39/001184; A61K 38/1735; A61K 38/1816; A61K 48/0075; A61K 38/28; A61K 48/0083; A61K 39/0011; A61K 48/0066; A61K 48/00; C12N 2310/31–337
See application file for complete search history.

(56) References Cited

U.S. PATENT DOCUMENTS 3,906,092 A    9/1975   Hilleman et al.
4,373,071 A    2/1983   Ltakura
(Continued)

FOREIGN PATENT DOCUMENTS

AU    776268        12/2000
CA    2854685       8/2002
(Continued)

OTHER PUBLICATIONS

Lu et al. Optimization of methods to achieve mRNA-mediated transfection of tumor cells in vitro and in vivo employing cationic liposome vectors. Cancer Gene Therapy, vol. 1, No. 4, pp. 245-252, Dec. 1994. (Year: 1994).*

(Continued)

*Primary Examiner* — Jennifer Dunston
(74) *Attorney, Agent, or Firm* — Parker Highlander PLLC

(57) ABSTRACT

The present invention relates to a pharmaceutical composition comprising a modified mRNA that is stabilised by sequence modifications and optimised for translation. The pharmaceutical composition according to the invention is particularly well suited for use as an inoculating agent, as well as a therapeutic agent for tissue regeneration. In addition, a process is described for determining sequence modifications that promote stabilisation and translational efficiency of modified mRNA of the invention.

19 Claims, 6 Drawing Sheets

Specification includes a Sequence Listing.

Related U.S. Application Data division of application No. 10/729,830, filed on Dec. 5, 2003, now Pat. No. 10,188,748, which is a continuation-in-part of application No. PCT/EP02/06180, filed on Jun. 5, 2002.

(51) Int. Cl.

| | | |
|---|---|---|
| A61K 47/54 | (2017.01) |
| A61K 47/64 | (2017.01) |
| A61K 38/19 | (2006.01) |
| A61K 39/00 | (2006.01) |
| C07K 14/005 | (2006.01) |
| C07K 14/47 | (2006.01) |
| G16B 20/50 | (2019.01) |
| A61K 39/145 | (2006.01) |
| A61K 39/108 | (2006.01) |
| C07K 14/245 | (2006.01) |
| C12N 7/00 | (2006.01) |
| C12N 15/11 | (2006.01) |
| A61K 38/18 | (2006.01) |
| A61K 38/28 | (2006.01) |
| A61K 39/12 | (2006.01) |
| A61K 39/21 | (2006.01) |
| A61K 38/17 | (2006.01) |
| G16B 20/00 | (2019.01) |
| G16B 30/00 | (2019.01) |

(52) U.S. Cl.
CPC .............. *G16B 20/00* (2019.02); *G16B 30/00* (2019.02); *Y02A 50/30* (2018.01)

(56) References Cited

U.S. PATENT DOCUMENTS

| | | |
|---|---|---|
| 4,401,796 A | 8/1983 | Ltakura |
| 4,415,732 A | 11/1983 | Caruthers et al. |
| 4,458,066 A | 7/1984 | Caruthers et al. |
| 4,500,707 A | 2/1985 | Caruthers et al. |
| 4,588,585 A | 5/1986 | Mark et al. |
| 4,668,777 A | 5/1987 | Caruthers et al. |
| 4,737,462 A | 4/1988 | Mark et al. |
| 4,816,567 A | 3/1989 | Cabilly et al. |
| 4,879,111 A | 11/1989 | Chong |
| 4,959,314 A | 9/1990 | Mark et al. |
| 4,973,679 A | 11/1990 | Caruthers et al. |
| 5,017,691 A | 5/1991 | Lee et al. |
| 5,047,524 A | 9/1991 | Andrus et al. |
| 5,091,309 A | 2/1992 | Schlesinger et al. |
| 5,116,943 A | 5/1992 | Koths et al. |
| 5,132,418 A | 7/1992 | Caruthers et al. |
| 5,153,319 A | 10/1992 | Caruthers et al. |
| 5,262,530 A | 11/1993 | Andrus et al. |
| 5,580,859 A | 12/1996 | Felgner et al. |
| 5,663,153 A | 9/1997 | Hutcherson et al. |
| 5,700,642 A | 12/1997 | Monforte et al. |
| 5,739,026 A | 4/1998 | Garoff et al. |
| 5,928,649 A | 7/1999 | Daley et al. |
| 5,965,720 A | 10/1999 | Gryaznov et al. |
| 5,965,726 A | 10/1999 | Pavlakis et al. |
| 6,214,804 B1 | 4/2001 | Felgner et al. |
| 6,239,116 B1 | 5/2001 | Krieg et al. |
| 6,265,387 B1 | 7/2001 | Mirus |
| 6,322,967 B1 | 11/2001 | Parkin |
| 6,376,248 B1 | 4/2002 | Hawley-Nelson et al. |
| 6,406,705 B1 | 6/2002 | Davis et al. |
| 6,413,942 B1 | 7/2002 | Felgner et al. |
| 6,500,919 B1 | 12/2002 | Adema et al. |
| 6,514,948 B1 | 2/2003 | Raz et al. |
| 6,552,006 B2 | 4/2003 | Raz et al. |
| 6,589,940 B1 | 7/2003 | Raz et al. |
| 6,602,705 B1 | 8/2003 | Barnett et al. |
| 6,610,661 B1 | 8/2003 | Carson et al. |
| 6,664,066 B2 | 11/2003 | Parks |
| 6,924,365 B1 | 8/2005 | Miller et al. |
| 6,943,015 B2 | 9/2005 | Frolov et al. |
| 7,001,890 B1 | 2/2006 | Wagner et al. |
| 7,208,478 B2 | 4/2007 | Carson et al. |
| 7,268,120 B1 | 9/2007 | Horton et al. |
| 7,276,489 B2 | 10/2007 | Agrawal et al. |
| 7,316,925 B2 | 1/2008 | Draghia-Akli et al. |
| 9,255,126 B2 | 2/2016 | Polo et al. |
| 10,188,748 B2 | 1/2019 | Von der Mülbe et al. |
| 10,568,972 B2 | 2/2020 | Von der Mülbe et al. |
| 2002/0123099 A1 | 9/2002 | Weiner et al. |
| 2002/0132788 A1 | 9/2002 | Lewis et al. |
| 2002/0142978 A1 | 10/2002 | Raz et al. |
| 2003/0008342 A1 | 1/2003 | Scholler et al. |
| 2003/0039636 A1 | 2/2003 | LeBoulch et al. |
| 2003/0077604 A1 | 4/2003 | Sun et al. |
| 2003/0083272 A1 | 5/2003 | Wiederholt et al. |
| 2003/0092145 A1 | 5/2003 | Jira et al. |
| 2003/0143204 A1 | 7/2003 | Lewis et al. |
| 2003/0143743 A1 | 7/2003 | Schuler et al. |
| 2003/0170273 A1 | 9/2003 | O'Hagan et al. |
| 2003/0225016 A1 | 12/2003 | Fearon et al. |
| 2004/0005667 A1 | 1/2004 | Ratti et al. |
| 2004/0009469 A1* | 1/2004 | Apt .................. C07K 14/005 435/5 |
| 2004/0029251 A1 | 2/2004 | Hoffman et al. |
| 2004/0106567 A1 | 6/2004 | Hagstrom et al. |
| 2004/0209274 A2 | 10/2004 | Daly |
| 2004/0259081 A1 | 12/2004 | Watzele et al. |
| 2005/0032730 A1 | 2/2005 | Schuler |
| 2005/0037494 A1 | 2/2005 | Hecker et al. |
| 2005/0059624 A1 | 3/2005 | Hoerr et al. |
| 2005/0064596 A1 | 3/2005 | Riemen et al. |
| 2005/0112141 A1 | 5/2005 | Terman |
| 2005/0250723 A1 | 11/2005 | Hoerr et al. |
| 2006/0172966 A1 | 8/2006 | Lipford et al. |
| 2006/0188490 A1 | 8/2006 | Hoerr et al. |
| 2006/0241076 A1 | 10/2006 | Uhlmann et al. |
| 2008/0025944 A1 | 1/2008 | Hoerr et al. |
| 2008/0171711 A1 | 7/2008 | Hoerr et al. |
| 2010/0303851 A1 | 12/2010 | Hoerr et al. |
| 2016/0194625 A1 | 7/2016 | Hoge et al. |
| 2019/0134222 A1 | 5/2019 | Von der Mülbe et al. |

FOREIGN PATENT DOCUMENTS

| | | |
|---|---|---|
| CA | 2473135 | 6/2003 |
| CA | 2376634 | 12/2005 |
| DE | 10119005 | 4/2001 |
| DE | 10229872 | 1/2004 |
| EP | 0175960 | 4/1986 |
| EP | 0839912 | 5/1998 |
| EP | 1083232 | 3/2001 |
| EP | 1393745 | 3/2004 |
| JP | 2000-509281 | 7/2000 |
| JP | 7-503372 | 2/2007 |
| WO | WO 1990/011092 | 10/1990 |
| WO | WO 1993/014778 | 8/1993 |
| WO | WO 1995/024485 | 9/1995 |
| WO | WO 1995/026204 | 10/1995 |
| WO | WO 1995/027069 | 10/1995 |
| WO | WO 1997/041210 | 11/1997 |
| WO | WO 1997/048370 | 12/1997 |
| WO | WO 1998/012207 | 3/1998 |
| WO | WO 1998/034640 | 8/1998 |
| WO | WO 1998/055495 | 12/1998 |
| WO | WO 1999/014346 | 3/1999 |
| WO | WO 1999/020774 | 4/1999 |
| WO | WO 1999/052503 | 10/1999 |
| WO | WO 2000/006723 | 2/2000 |
| WO | WO 2000/029561 | 5/2000 |
| WO | WO 2000-039304 | 7/2000 |
| WO | WO 2000/057910 | 10/2000 |
| WO | WO 2000/075304 | 12/2000 |
| WO | WO 2001/004313 | 1/2001 |
| WO | WO 2001/014416 | 3/2001 |
| WO | WO 2001/021810 | 3/2001 |
| WO | WO 2001/093902 | 12/2001 |

(56) References Cited

FOREIGN PATENT DOCUMENTS

| | | |
|---|---|---|
| WO | WO 2002/008435 | 1/2002 |
| WO | WO 2002/064799 | 8/2002 |
| WO | WO 2002/098443 | 12/2002 |
| WO | WO 2003/028656 | 4/2003 |
| WO | WO 2003/051401 | 6/2003 |
| WO | WO 2003/059381 | 7/2003 |
| WO | WO 2003/066649 | 8/2003 |
| WO | WO 2003/066868 | 8/2003 |
| WO | WO 2003/086280 | 10/2003 |
| WO | WO 2004/058159 | 7/2004 |
| WO | WO 2004/092329 | 10/2004 |
| WO | WO 2006/008154 | 1/2006 |
| WO | WO 2006/024518 | 3/2006 |
| WO | WO 2007/024708 | 3/2007 |

OTHER PUBLICATIONS

Gen Bank Accession No. BAA00394.1, polyprotein precursor, partial [Dengue virus type 1], publicly available Feb. 2000, printed as p. 1/1. (Year: 2000).*

Gen Bank Accession No. D00502.1, Dengue virus type 1 (strain Thailand AHF82-80) gene for polyprotein precursor, partial cds (C, PreM, M, E, NS1 region), publicly available Feb. 2000, printed as pp. 1/2-2/2. (Year: 2000).*

Weissman, D. mRNA transcript therapy. Expert Review of Vaccines, vol. 14, No. 2, pp. 265-281, 2015, published online Oct. 31, 2014. (Year: 2014).*

Ishii et al. TLR Ignores Methylated RNA? Immunity, vol. 23, No. 2, pp. 111-114, Aug. 2005. (Year: 2005).*

Gallie. The cap and poly(A) tail function synergistically to regulate mRNA translational efficiency. Genes & Development, vol. 5, pp. 2108-2116, 1991. (Year: 1991).*

Aissani et al., "CpG islands, genes and isochores in the genomes of vertebrates," *Gene*, 106:185-195, 1991.

Akashi, "Gene expression and molecular evolution," *Curr. Opin. Genet. Dev.*, 11 (6):660-666, 2001.

Alberts et al., *Molecular Biology of the Cell*, 3rd Ed., Garland Publishing, Inc. New York, NY, pp. 368-369, 1994.

Altschul et al., "Gapped BLAST and PSI-BLAST: a new generation of protein database search programs," *Nucleic Acids Res.*, 25(17):3389-3402, 1997.

Anichini et al., "Cytotoxic T cells directed to tumor antigen not expressed on normal melanocytes dominate HLA-A2 1-restricted immune repertoire to melanoma," *J Immunol.*, 156(1):208-217, 1996.

Aota et al., "Diversity in G+C content at the third position of codons in vertebrate genes and its cause," *Nucleic Acids Research*, 14(16):6345-6356, 1986.

Apostolopoulos et al., "Cellular mucins: targets for immunotherapy," *Crit Rev Immunol.*, 14(3-4):293-309, 1994.

Ashley et al., "Bone marrow-generated dendritic cells pulsed with tumor extracts or tumor RNA induce antitumor immunity against central nervous system tumors," *J Exp Med.*, 186(7): 1177-1182, 1997.

Aurup et al., "Translation of 2'~modified mRNA in vitro and in vivo," *Nucleic Acids Research*, 22(23):4963-4968, 1994.

Austyn, "New insights into the mobilization and phagocytic activity of dendritic cells," *J Exp Med.*, 183(4): 1287-1292, 1996.

Bernardi, "Isochores and the evolutionary genomics of vertebrates," *Gene*, 241:3-17, 2000.

Bernardi, "The vertebrate genome: isochores and evolution," *Mol. Biol. Evol.* 10:186-204, 1993.

Berneman et al., "T-Cell Stimulatory Capacity of Different Types of In Vitro Cultured Monocyte-Derived Dendritic Cells Following Electroporation with RNA Encoding Defined Antigens," Laboratory of Experimental Hematology, University of Antwerp, 1(11), Abstract No. 5536, Nov. 16, 2002.

Bernhard et al., "Generation of immunostimulatory dendritic cells from human CD34+ hematopoietic progenitor cells of the bone marrow and peripheral blood," *Cancer Res.*, 55(5):1099-1104, 1995.

Bettinger et al., "Peptide-mediated RNA delivery: a novel approach for enhanced transfection of primary and post-mitotic cells," *Nucleic Acids Research*, 29(18):3882-3891, 2001.

Bevan, "Antigen presentation to cytotoxic T lymphocytes in vivo," *J Exp Med*, 182(3):639-641, 1995.

Bevilacqua et al., "Post-transcriptional regulation of gene expression by degradation of messenger RNAs," *Journal of Cellular Physiology*, 195(3):356-372, 2003.

Bieler und Wagner (in: Schleef), Plasmids for Therapy and Vaccination, Kapitel 9, Seiten 147-168, Wiley-VCH, Weinheim, 2001.

Binder et al., "Evidence that the pathway of transferrin receptor mRNA degradation involves an endonucleolytic cleavage within the 3' UTR and does not involve poly(A) tail shortening," *EMBO J.*, 13(8):1969-1980, 1994.

Bird, "CpG-tich islands and the function of DNA methylation," *Nature*, 321:209-213, 1986.

Boczkowski et al., "Dendritic cells pulsed with RNA are potent antigen-presenting cells in vitro and in vivo," *J. Exp. Med.*, 184:465-472, 1996.

Boczkowski et al., "Induction of tumor immunity and cytotoxic T lymphocyte responses using dendritic cells transfected with messenger RNA amplified from tumor cells," *Cancer Res.*, 60(4):1028-1034, 2000.

Boon et al., "Genes coding for tumor rejection antigens: perspectives for specific immunotherapy," *Important Adv Oncol*, 53-69, 1994.

Boyum, "Separation of white blood cells," *Nature*, 204:793-794, 1964.

Brandt et al., "Detection of the metastatic potential of blood-borne and immunomagnetically enriched epithelial cells by quantitative erbB-2 RT-PCR," *Clin. Exp. Metastasis*, 14:399-408, 1996.

Brossart et al., "Her-2/neu-derived peptides are tumor-assocated antigens expressed by human renal cell and colon carcinoma lines and are recognized by in vitro induced specific cytotoxic T lymphocytes," *Cancer Res.*, 58(4):732-736, 1998.

Brossart et al., "Identification of HLA-A2-restricted T-cell epitopes derived from the MUC1 tumor antigen for broadly applicable vaccine therapies," *Blood*, 93(12):4309-4317, 1999.

Brossart et al., "Induction of CTL responses in vivo after vaccinations with peptide pulsed dendritic cells," *Blood*, 96:3102-3108, 2000.

Brossart et al., "Virus-mediated delivery of antigenic epitopes into dendritic cells as a means to induce CTL," *J Immunol*, 158(7):3270-3276, 1997.

Cannon et al., "RNA Based Vaccines," *DNA and Cell Biology*, 21(12): 953-961, 2002.

Caput et al., "Identification of a common nucleotide sequence in the 3'-untranslated region of mRNA molecules specifying inflammatory mediators," *Proc. Natl. Acad. Sci. USA*, 83:1670-1674, 1986.

Caron et al., "The human transcriptome map: clustering of highly expressed genes in chromosomal domains," *Science*, 291:1289, 2001.

Carralot et al., "Polarization of immunity induced by direct injection of naked sequence-stabilized mRNA vaccines," *Cell Mol Life Sci*, 61(18):2418-2424, 2004.

Carralot et al., "Production and characterization of amplified tumor-derived cRNA libraries to be used as vaccines against metastatic melanomas," *Genetic Vaccines and Therapy*, 3(6):1-10, 2005.

CD154, Wikipedia, the free encyclopedia, Jun. 25, 2010.

Celluzi et al., "Peptide-pulsed dendritic cells induce antigen-specific CTL-mediated protective tumor immunity," *J Exp Med*, 183(1):283-287, 1996.

Chen et al., "Enhanced protection against a lethal influenza virus challenge by immunization with both hemagglutinin- and neuraminidase-expressing DNAs," *Vaccine*, 17(7-8):653-659, 1999.

Cheng et al., "Enhancement of Sindbis virus self-replicating RNA vaccine potency by linkage of Herpes simplex virus type 1 VP22 protein to antigen," *J. Virol.*, 75(5):2368-2376, 2001.

(56) References Cited

OTHER PUBLICATIONS

Cho et al., "Enhanced cellular immunity to hepatitis C virus non-structural proteins by codelivery of granulocyte macrophage-colony stimulating factor gene in intramuscular DNA immunization," *Vaccine*, 17(9-10):1136-1144, 1999.
Cohen et al., "Murine epidermal Langerhans cells and splenic dendritic cells present tumor-associated antigens to primed T cells," *Eur J Immunol.*, 24(2):315-319, 1994.
Colot and Rossignol, "Eukaryotic DNA methylation as an evolutionary device," *BioEssays*, 21:402-411, 1999.
Conry et al., "Characterization of a messenger RNA polynucleotide vaccine vector," *Cancer Research*, 55(7):1397-1400, 1995.
Coughlin et al., "Targeting adult and pediatric cancers via cell-based vaccines and the prospect of activated B lymphocytes as a novel modality," *Cancer Biology & Therapy*, 2(5):466-470, 2003.
Craig and Bickmore, "The distribution of CpG islands in mammalian chromosomes," *Nature Genetics*, 7:376-382, 1994.
Cramer et al., "Functional association between promoter structure and transcript alternative splicing," *PNAS*, 94:11456-11460, 1997.
Culver et al., Gene Therapy, A Handbook for Physicians, pp. 63-77, 1994.
Database Corenucleotide, NCBI Database accession No. AF033819, Aug. 2002.
Database Geneseq, Database accession No. AAV21762, Jul. 1998.
Deres el al., "In vivo priming of virus-specific cytotoxic T lymphocytes with synthetic lipopeptide vaccine," *Nature*, 342:561-564, 1989.
Deshayes et al., "Cell-penetrating peptides: tools for intracellular delivery of therapeutics," *Cell Mol Life Sci*, 62(16):1839-1849, 2005.
Diebold et al., "Innate antiviral responses by means of TLR7-mediated recognition of single-stranded RNA," *Science*, 303(5663):1529-1531, 2004.
Disbrow et al., "Codon optimization of thee HPV~16 E5 gene enhances protein expression," *Virology*, 311:105-114, 2003.
Donnelly et al., "Technical and regulatory hurdles for DNA vaccines," *Int J Parasitol*, 33(5-6):457-467, 2003.
Dunham, "The application of nucleic acid vaccines in veterinary medicine," *Res Vet Sci.*, 73(1):9-16, 2002.
Duret el al., "Expression pattern and, surprisingly, gene length shape codon usage in *Caenorhabditis, Drosophila, and Acabidopsis,*" *Proc, Nat. Acad. Sci. USA*, 96:4482-4487, 1999.
Duret, "Evolution of synonymous codon usage in metazoans," *Current Opinion in Genetics & Development*, 12:640-648, 2002.
Edelstein et al., "Gene therapy clinical trials worldwide 1989-2004—an overview," *J Gene Med.*, 6(6):597-602, 2004.
Egeter et al., "Eradication of Disseminated Lvmphomas with CpG-DNA Activated T Helper Type 1 Cells from Nontransgenio Mice," *Cancer Research*, 60(6):1515-1520, 2000.
Elbashir et al., "Duplexes of 21-nucleotide RNAs mediate RNA interference in cultured mammalian cells," *Nature*, 411(6836):494-498, 2001.
Fang et al., "Functional Measurement of Hepatitis C Virus Core-Specific CD8+ T-Cell Responses in the Livers or Peripheral Blood of Patients bv Using Autologous Peripheral Blood Mononuclear Cells as Targets or Stimulators," *Journal of Clinical Microbiology*, 39(11):3985-3901, 2001.
Fearnley et al., "Monitoring human blood dendritic cell numbers in normal individuals and in stem cell transplantation," *Blood*, 93(2):728-736, 1999.
Fisch et al., "Generation of antigen-presenting cells for soluble protein antigens ex vivo from peripheral blood CD34+ hematopoietic progenitor cells in cancer patients," *Eur J Immunol.*, 26(3):595-600, 1996.
Fisk et al., "Identification of an immunodominant peptide of HER-2/neu protooncogene recognized by ovarian tumor-specific cytotoxic T lymphocyte lines," *J Exp Med*, 161(6):2109-2117, 1995.
Fisk et al., "Identification of an immunodominant peptide of HER-2/neu protooncogene recognized bv ovarian tumor-specific cytotoxic T lymphocyte lines," *J Exp Med*, 181(6):2109-2117, 1995.
Ford et al., "The poly(A) tail inhibits the assembly of a 3'-to5' exonuclease in an in vitro RNA stability system," *Molecular and Cellular Biology*, 17(1):398-406, 1997.
Fynan et al., "DNA vaccines: protective immunization by parenteral, mucosal, and gene-gun inoculations," *Proc Natl Acad Sci USA*, 90(24):11478-11482, 1993.
Gao et al., "Nonviral gene delivery: what we know and what is next," *AAPS J*, 9(1):E92-E104, 2007.
Garbe et al., "Epidemiology of malignant melanoma in West Germany in an international comparison," *Onkologie*, 12(6):253-262, 1989.
Gardiner-Garden et al., "CpG islands in vertebrate genomes," *J. Mol. Biol.*, 196:261-282, 1987.
GenBank Accession No. AF125673, GI: 4927719, Jun. 2000.
GenBank Accession No. X65300, "Cloning vector pGEM-1," 1999.
GenBank Accession No. X65327, "Cloning vector pSP64," 1999.
GenBank: U26404, 1996, and Lai et al., "Patterning of the neural ectoderm of Xenopus laevis by the amino-terminal product of hedgehog autoproteoltic cleavage," *Development*, 121(8):2349-2360, 1995.
GenBank: X65300, 1999, "Cloning vector pGEM-1," Technical Services, Promega Corporation, May 28, 1993.
GenBank: X65327, 1999, "Cloning vector pSP64," Technical Services, Promega Corporation, Mar. 23, 1992.
Gilkeson et al., "Induction of cross-reactive anti-dsDNA antibodies in preautoimmune NZB/NZW mice by immunization with bacterial DNA," *J Clin Invest*, 95(3):1398-1402, 1995.
Grabbe et al., "Dendritic cells as initiators of tumor immune responses: a possible strategy for tumor immunotherapy," *Immunol Today*, 16(3):117-121, 1995.
Grabbe et al., "Tumor antigen presentation by epidermal antigen-presenting cells in the mouse: modulation by granulocyte-macrophage colony-stimulating factor, tumor necrosis factor alpha, and ultraviolet radiation," *J Leukoc Biol*, 52(2):209-217, 1992.
Grabbe et al., "Tumor antigen presentation by murine epidermal cells," *J Immunol*, 146(10):3656-3661, 1991.
Graham et al., "Intramuscular immunization with MUC1 cDNA can protect C57 mice challenged with MUC1-expressing syngeneic mouse tumor cells," *International Journal of Cancer*, 65:664-667, 1996.
Gram et al., "Immunological analysis of a Lactococcus lactis-based DNA vaccine expressing HIV gp120," *Genetic Vaccine and Therapy*, 5(3):1/11-11/11, 2007.
Granstein et al., "Induction of anti-tumor immunity with epidermal cells pulsed with tumor-derived RNA or intradermal administration of RNA," *J Invest Dermatol.*, 114(4):632-636, 2000.
Gryaznov, "Oligonucleotide N3'>P5' phosphoramidates as potential therapeutic agents," *Biochim Biophys Acta.*, 1489(1):131-140, 1999.
Haas et al., "Codon usage limitation in the expression of HIV-1 envelope glycoprotein," *Current Biology*, 6(3):315-324, 1996.
Heidenreich et al., "Chemically modified RNA: approaches and applications," *FASEB Journal*, 7(1):90-96, 1993.
Heil et al., "Species-specific recognition of single-stranded RNA via toll-like receptor 7 and 8," *Science*, 303(5663):1526-1529, 2004.
Heiser et al., "Autologous dendritic cells transfected with prostate-specific antigen RNA stimulate CTL responses against metastatic prostate tumors," *Journal of Clinical Investigation*, 109(3):409-417, 2002.
Heiser et al., "Human dendritic cells transfected with renal tumor RNA stimulate polyclonal T-cell responses against antigens expressed by primary and metastatic tumors," *Cancer Research*, 61(8):3388-3393, 2001.
Heiser et al., "Human dendritic cells transfected with RNA encoding prostate-specific antigen stimulate prostate-specific CTL responses in vitro," *Journal of Immunology*, 164(10):5508-5514, 2000.
Heiser et.al., "Induction of polyclonal prostate cancer-specific CTL using dendritic dells transfected with amplified tumor RNA," *J. Immunol.*, 166(5):2953-2960, 2001.
Hemmi et al., "A toll-like receptor recognizes bacterial DNA," *Nature*, 408:740-745, 2000.
Herweijer et al., "Gene therapy progress and prospects: Hydrodynamic gene delivery, " *Gene Ther.*, 14(2):99-107, 2007.

(56) References Cited

OTHER PUBLICATIONS

Hilleren et al., "Mechanisms of mRNA surveillance in eukaryotes," *Annu Rev Genet.*, 3:229-260, 1999.
Hirasawa, "Natural autoantibody to MUC1 is a prognostic indicator for non-small cell lung cancer," *American Journal of Respiratory and Critical Care Medicine*, 161:589-594, 2000.
Hoath et al., "The Organization of Human Epidermis: Functional Epidermal Units and Phi Proportionality," *J. Invest. Dermatol.*, 121:1440-1446, 2003.
Hoerr et al., "In vivo application of RNA leads to induction of specific cytotoxic T lymphocytes and antibodies," *Eur. J. Immunol.*, 30(1):1-7, 2000.
Holcik el al., "Four highlv stable eukaryotic mRNAS assemble 3' untranslated region RNA-protein complexes sharing cis and trans components," *Proc Natl Acad Sci USA*, 94(6):2410-2414, 1997.
Holmes and Morgan, "Cell positioning and sorting using dielectrophoresis," *European Cells and Materials*, 4(Suppl. 2):120-122, 2002.
Houghton et al., "Cancer antigens: immune recognition of self and altered self," *J Exp Med*, 180(1):1-4, 1994.
Hsu et al., "Vaccination of patients with B-cell lymphoma using autologous antigen-pulsed dendritic cells," *Nat Med*, 2(1):52-58, 1996.
Huddleston et al., "The sequence of the nucleoprotein gene of human influenza A virus, strain a/NT/60/68," *Nucleic Acids Research*, 10(3):1029-1038, 1982.
Inaba et al., "Dendritic cells pulsed with protein antigens in vitro can prime antigen-specific, MHC-restricted T cells in situ," *J Exp Med*, 172(2):631-640, 1990.
Inaba et al., "Direct activation of CD8+ cytotoxic T lymphocytes by dendritic cells," *J Exp Med*, 166(1):182-194, 1987.
Iwasaki et al., "Enhanced CTL responses mediated by plasmid DNA immunogens encoding costimulatory molecules and cytokines," *J Immunol.*, 158(10:4591-4601, 1997.
Janeway et al., Immunobiology, The Immune System in Health and Disease, 13:12-13:21, 1997.
Janssens et al., "Role of Toll-Like Receptors in Pathogen Recognition," *Clinical Microbiology Reviews*, 16(4):637-646, 2003.
Januszyk and Lima, "Structural components and architectures of RNA exosomes," in: Madame Curie Bioscience Database, Landes Bioscience, downloaded at http://www.ncbi.nlm.nih.gov/books/NBK45033/, 22 pages, 2000.
Kabanov et al., "A new class of antivirals: antisense oligonucleotides combined with a hydrophobic substituent effectively inhibit influenza virus reproduction and synthesis of virus-specific proteins in MDCK cells," *FEBS Lett*, 259(2): 327-330, 1990.
Kalnins et al., "Sequence of the lacZ gene of *Escherichia coli,*" *EMBO J.*, 2(4): 593-597, 1983.
Kanaya et al., "Codon usage and tRNA genes in eukaryotes: correlation of codon usage diversity with translation efficiency and with CG-dinucleotide usage as assessed by multivariate analysis," *J Mol Evol*, 53:290-298, 2001.
Kandimalla et al., "Divergent synthetic nucleotide motif recognition pattern: design and development of potent immunomodulatory oligodeoxyribonucleotide agents with distinct cytokine induction profiles," *Nucleic Acids Research*, 31(9):2393-2400, 2003.
Kandimallia et al., "Immunomodulatory oligonucleotides containing a cytosine-phosphate-2'-deoxy-7-deazaguanosine motif as potent toll-like receptor 9 agonists," *PNAS*, 102(19):6925-6930, 2005.
Kariko et al., "Suppression of RNA Recognition by Toll-like Receptors: The Impact of Nucleoside Modification and the Evolutionary Origin of RNA," *Immunity*, 23:165-175, 2005.
Karlin et al., "Applications and statistics for multiple high-scoring segments in molecular sequences," *Proc Natl Acad Sci USA*, 90(12):5873-5877, 1993.
Kim et al., "Codon optimization for high-level expression of human erythropoietin (EPO) in mammalian cells," *Gene*, 199:293-301, 1997.
Klinmann et al., "DNA vaccines safety and efficacy issues," *Springer Semin Immunopathol*, 19(2):245-256, 1997.

Kohler et al., "Continuous cultures of fused cells secreting antibody of predefined specificity," *Nature*, 256(5517):495-497, 1975.
Koide et al., "DNA Vaccines," *Jpn J. Pharmacol.*, 83(3)167-174, 2000.
Koido et al., "Induction of antitumor immunity by vaccination of dendritic cells transfected with MUC1 RNA," *J Immunol*, 165(10:5713-5719, 2000.
Komar et al., "Synonymous codon substitutions affect ribosome traffic and protein folding during in vitro translation," *FEBS Letters*, 462:387-391, 1999.
Kontermann, "Recombinant bispecific antibodies for cancer therapy," *Acta Pharmacol Sin*, 26(1):1-9, 2005.
Krieg et al., "In vitro RNA synthesis with SP6 RNA polymerase," *Methods Enzymol*, 155:397-415, 1987.
Kudla et al., "High Guanine and Cytosine Content Increases mRNA Levels in Mammalian Cells," *PLoS Biol*, 4(6):e180, 2006.
Kufe et al., Cancer Medicine, 6th edition, Table 12-1, 2003.
Kugler et al., "Regression of human metastatic renal cell carcinoma after vaccination with tumor cell-dendritic cell hybrids," *Nat Med*, 6(3):332-336, 2000.
Kundu and Rao, "CpG islands in chromatin organization and gene expression," *J. Biochem.*, 125:217-222, 1999.
Kusakabe et al., "The timing of GM-CSF expression plasmid administration influences the Th1/Th2 response induced by an HIV-1 specific DNA vaccine," *J Immunol*, 164(6):3102-3111, 2000.
Kwissa et al., "Cytokine-facilitated priming of CD8+ T cell responses by DNA vaccination," *J Mol Med*, 81(2):91-101, 2003.
Larregina et al., "Changing Paradigms in Cutaneous Immunology: Adapting with Dendritic Cells," *The Journal of Investigative Dermatology*, 124(1):1-12, 2005.
Lathe, "Synthetic oligonucleotide probes deduced from amino acid sequence data Theoretical and practical considerations," *Journal of Molecular Biology*, 183(1):1-12, 1985.
Lee et al., "Molecular basis for the immunostimulatory activity of guanine nucleoside analogs: Activation of Toll-like receptor 7" *PNAS*, 100(11):6646-6651, 2003.
Leitner et al., "DNA and RNA-based vaccines: principles, progress and prospects," *Vaccine*, 18(9-10):765-777, 2000.
Lenz et al., "Human and murine dermis contain dendritic cells. Isolation bv means of a novel method and phenotypical and functional characterization," *Journal of Clinical Investigation*, 92:2587-2596, 1993.
Linehan et al., "Tumor-specific and HLA-A2-restricted cytolysis by tumor-associated lymphocytes in human metastatic breast cancer," *J Immunol*, 155(9):4486-4491, 1995.
Loging et al., "Identifying potential tumor markers and antigens by database mining and rapid expression screening," *Genome Res.*, 10:1393-1402, 2000.
Lopez-Ferrer et al., "Mucins as differentiation markers in bronchial epithelium," *American Journal of Respiratory Cell and Molecular Biology*, 24(1):22-29, 2001.
Luo et al., "Synthetic DNA delivery systems," *Nat Biotechnol.*, 18(1):33-37, 2000.
Martinon el al., "Induction of virus-specific cytotoxic T lymphocytes in vivo by liposome-entrapped mRNA," *Eur J Immunol.*, 23(7):1719-1722, 1993.
Mathers et al., "Professional antigen-presenting cells of the skin," *Immunol. Res.*, 36(1-3):127-136, 2006.
Matray et al., "Synthesis and properties of RNA analogs—oligoribonucleotide N3' > P5' phosphoramidates," *Nucleic Acids Research*, 27(20):3976-3985, 1999.
McCafferty et al., "Phage antibodies: filamentous phage displaying antibody variable domains," *Nature*, 348(6301):552-554, 1990.
McKenzie et al., "Nucleic acid vaccines: tasks and tactics," *Immunologic Research*, 24(3):225-244, 2001.
Meunier et al., "Heterogeneous populations of class II MHC+ cells in human dermal cell suspensions. Identification of a small subset responsible for potent dermal antigen-presenting cell activity with features analogous to Langerhans cells," *The Journal of Immunology*, 151(8):4067-4080, 1993.

(56) References Cited

OTHER PUBLICATIONS

Minks et al., "Structural Requirements of Double-stranded RNA for the Activation of 2',5'-oligo(A) Polymerase and Protein. Kinase of Interferon-treated HeLa Cells," *The Journal of Biological Chemistry*, 254(20):10180-10183, 1979.
Mishra et al., "Improved leishmanicidal effect of phosphorotioate antisense oligonucleotides by LDL-mediated delivery," *Biochim Biophys Acta*, 1264(2):229-237, 1995.
Mitchell et al., "mRNA turnover," *Curr Opin Cell Biol.*, 13(3):320-325, 2001.
Mitchell et al., "RNA-transfected dendritic cells in cancer immunotherapy," *J Clin Invest*, 106(9):1065-1069, 2000.
Morinaga et al., "Primary structures of human a-fetoprotein and its mRNA," *Proc. Natl. Acad. Sci. USA*, 80:4604-4608, 1983.
Morse et al., "Generation of dendritic cells in vitro from peripheral blood mononuclear cells with granulocyte-macrophage-colony-stimulating factor, interleukin-4, and tumor necrosis factor-alpha for use in cancer immunotherapy," *Annals of Surgery*, 226:6-16, 1997.
Müller et al., "Transfection of dendritic cells with RNA induces CD4- and CD8-mediated T cell immunity against breast carcinomas and reveals the immunodominance of presented T cell epitopes," *J Immunol*, 170(12):5892-5896, 2003.
Nagata et al., "Codon optimization effect on translational efficiency of DNA vaccine in mammalian cells: analysis of plasmid DNA encoding a CTL epitope derived from microorganisms," *Biochemical and Biophysical Research Communications*, 261:445-451, 1999.
Nair et al., "Antigen-presenting cells pulsed with unfractionated tumor-derived peptides are potent tumor vaccines," *Eur J Immunol*, 27(3):589-597, 1997.
Nair et al., "Induction of cytotoxic T cell responses and tumor immunity against unrelated tumors using telomerase reverse transcriptase RNA transfected dendritic cells," *Nat Med*, 6(9):1011-1017, 2000.
Nair et al.. "Induction of primary carcinoembryonic antigen (CEA)— specific cytotoxic T lymphocytes in vitro using human dendritic cells transfected with RNA," *Nat Biotechnol*, 16(4)364-369, 1998.
Nair et al., "Soluble proteins delivered to dendritic cells via pH-sensitive liposomes induce primary cytotoxic T lymphocyte responses in vitro," *J Exp Med*, 175(2):609-612, 1992.
Nestle et al., "Vaccination of melanoma patients with peptide-or tumor lysate-pulsed dendritic cells," *Nat Med*, 4(3):328-332, 1998.
Nicholson el al., "Accurate in vitro cleavage by RNase III of phosphorothioate-substituted RNA processing signals in bacteriophage T7 early mRNA," *Nucleic Acids Research*, 16(4):1577-1591, 1988.
O'Doherty et al., "Human blood contains two subsets of dendritic cells, one immunologically mature and the other immature," *Immunology*, 82:487-493, 1994.
Oberhauser et al., "Effective incorporation of 2'-O-methyl-oligoribonucleotides into liposomes and enhanced cell association through modification with thiocholesterol," *Nucleic Acids Res*, 20(3):533-538, 1992.
Office Action issued in U.S. Appl. No. 10/729,830, dated Aug. 17, 2010.
Office Action issued in U.S. Appl. No. 10/729,830, dated Apr. 14, 2008.
Office Action issued in U.S. Appl. No. 10/729,830, dated Apr. 17, 2006.
Office Action issued in U.S. Appl. No. 10/729,830, dated Aug. 25, 2005.
Office Action issued in U.S. Appl. No. 10/729,830, dated Aug. 28, 2007.
Office Action issued in U.S. Appl. No. 10/729,830, dated Dec. 23, 2008.
Office Action issued in U.S. Appl. No. 10/729,830, dated Jun. 1, 2005.
Office Action issued in U.S. Appl. No. 10/729,830, dated Jun. 23, 2014.
Office Action issued in U.S. Appl. No. 10/729,830, dated Jun. 19, 2007.

Paglia et al., "Murine dendritic cells loaded in vitro with soluble protein prime cytotoxic T lymphocytes against tumor antigen in vivo," *J Exp Med*, 183(1):317-322, 1996.
Palu et al., "In pursuit of new developments for gene therapy of human diseases," *J. Biotechnol.*, 68(1)1-13, 1999.
Palucka et al., "Taming cancer by inducing immunity via dendritic cells," *Immunological Reviews*, 220:129-150, 2007.
Peoples et al., "Breast and ovarian cancer-specific cytotoxic T lymphocytes recognize the same HER2/neu-derived peptide," *Proc Natl Acad Sci USA*, 92(2):432-436, 1995.
Pesole et al., "UTRdb and UTRsite: specialized databases of sequences and functional elements of 5' and 3' untranslated regions of eukaryotic mRNAs," *Nucleic Acids Res.*, 30(1):335-340, 2002.
Ponsaerts et al., "Cancer immunotherapy using RNA-loaded dendritic cells," *Clinical and Experimental Immunology*, 134:378-384, 2003.
Porgador et al., "Bone marrow-generated dendritic cells pulsed with a class I-restricted peptide are potent inducers of cytotoxic T lymphocytes," *J Exp Med*, 182(1):255-260, 1995.
Porgador et al., "Induction of antitumor immunity using bone marrow-generated dendritic cells," *J Immunol.*, 156(8):2918-2926, 1996.
Rajagopalan et al., "Turnover and Translation of in Vitro Synthesized Messenger RNAs in Transfected, Normal Cells." *The Journal of Biological Chemistry*, 271(33):19871-19876, 1996.
Ramazeilles et al., "Antisense phosphorothioate oligonucleotides: selective killing of the intracellular parasite Leishmania amazonensis," *Proc. Natl. Acad. Sci. USA*, 91:7859-7863, 1994.
Rammensee et al., "Peptides naturally presented by MHC class I molecules," *Annu Rev Immunol*, 11:213-244, 1993.
Renkvist et al., "A listing of human tumor antigens recognized by T cells," *Cancer Immunol Immunother.*, 50:3-15, 2001.
Reyes-Sandoval et al., "DNA vaccines," *Current Molecular Medicine*, 1:217-243, 2001.
Robbins el al., "Human tumor antigens recognized by T cells," *Curr Opin Immunol*, 8(5):628-636, 1996.
Robinson et al., "Expression of Human nPTB is Limited by Extreme Suboptimal Codon Content," *PLoS One*, 3(3): e1801, 2008.
Robinson et al.. "Protection against a lethal influenza virus challenge by immunization with a haemagglutinin-expressing plasmid DNA," *Vaccine*, 11(9):957-960, 1993.
Rock, "A new foreign policy: MHC class I molecules monitor the outside world," *Immunol Today*, 17(3):131-137, 1996.
Roitt et al., *Immunology*, 4$^{th}$ Edition. Barcelona: Times Mirror International Publishers Limited, p. 1.7, 1996.
Romani et al., "Generation of mature dendritic cells from human blood. An improved method with special regard to clinical applicability," *Journal of Immunological Methods*, 196:137-151, 1996.
Romani et al., "Presentation of exogenous protein antigens by dendritic cells to T cell clones. Intact protein is presented best by immature, epidermal Langerhans cells," *J Exp Med*, 169(3):1169-1178, 1989.
Rosenberg et al., "Cancer immunotherapy: moving beyond current vaccines," *Nat Med*, 10(9):909-915, 2004.
Ross et al., "Control of messenger RNA stability in higher eukaryotes," *Trends Genet.*, 12(5):171-175, 1996.
Saenz-Badillos et al., "RNA as a tumor vaccine: a review of the literature," *Exp. Dermatol.*, 10(3):143-154, 2001.
Saison-Behmoaras et al., "Short modified antisense oligonucleotides directed against Ha-ras point mutation induce selective cleavage of the mRNA and inhibit T24 cells proliferation," *Embo J*, 10(5):1111-1118, 1991.
Sakatsume et al., "Inhibitory effect of oligoribonucleotide phosphorodithioates against the 3'-exonuclease activity," *Nucleic Acids Symposium Series*, 27:195-196, 1992.
Sallusto et al., "Dendritic cells use micropinocytosis and the mannose receptor to concentrate macromolecules in the major histocompatibility complex class II compartment: downregulation by cytokines and bacterial products," *J Exp Med*, 182(2):389-400, 1995.
Sallusto et al., "Efficient presentation of soluble antigen by cultured human dendtitic cells is maintained by granulocyte/macrophage

(56) References Cited

OTHER PUBLICATIONS colony-stimulating factor plus interleukin 4 and downregulated by tumor necrosis factor alpha," *Journal of Experimental Medicine*, 179(4):1109-1118, 1994.
Satthaporn et al., "Dendritic cells (II): Role and therapeutic implications in cancer," *J.R. Coll. Surg. Edinb.*, 46(3)159-167, 2001.
Scheel et al., "Immunostimulating capacities of stabilized RNA molecules," *Eur J Immunol*, 34(2):537-547, 2004.
Schirmacher et al., "Intra-pinna anti-tumor vaccination with self-replicating infectious RNA or with DNA encoding a model tumor antigen and a cytokine," *Gene Therapy*, 7(13)1137-1147, 2000.
Schmitt et al., "In vitro induction of a bladder cancer-specific T-cell response by mRNA-transfected dendritic cells," *J Cancer Res Clin Oncol*, 127(3):203-206, 2001.
Schuler et al., "Murine epidermal Langerhans cells mature into potent immunostimulatory dendritic cells in vitro," *J Exp Med*, 161(3):526-546, 1985.
Schuler-Thurner et al., "Mage-3 and influenza-matric peptide-specific cytotoxic T cells are inducible in terminal stage HLA-A2 1+ melanoma patients by mature monocyte-derived dendritic cells," *J Immunol.*, 165(6):3492-3496, 2000.
Sharp et al., "DNA sequence evolution: the sounds of silence," *Phil. Trans. R. Soc. Land. B*, 349:241-247, 1995.
Shea et al., "Synthesis, hybridization properties and antiviral activity of lipid-oligodeoxynucleotide conjugates," *Nucleic Acids Res*, 18(13):3777-3783, 1990.
Siena et al., "Expansion of Immunostimulatory Dendritic Cells from Peripheral Blood of Patients with Cancer," *The Oncologist*, 2:65-69, 1997.
Sousa, "Use of T7 RNA Polymerase and Its Mutants for Incorporation of Nucleoside Analogs into RNA," *Methods in Enzymology*, 317:65-74, 2000.
Steinman et al., "Dendritic cells: antigen presentation, accessory function and clinical relevance," *Adv Exp Med Biol*, 329:1-9, 1993.
Steinman, "The dendritic cell system and its role in immunogenicity," *Annu Rev Immunol.*, 9:271-296, 1991.
Sterner and Berger, "Acetylation of histones and transcription-related factors," *Microbiology and Molecular Biology Reviews*, 64(2):435-459, 2000.
Stinchcomb et al., "Isolation and characterisation of a yeast chromosomal replicator," *Nature*, 282(5734): 39-43, 1979.
Strong et al., "Incorporation of β-globin untranslated regions into Sindbis virus vector for augmentation of heterologous mRNA expression," *Gene Therapy*, 624-627, 1997.
Su et al., "Enhanced induction of telomerase-specific CD4(+) T cells using dendritic cells transfected with RNA encoding a chimeric gene product," *Cancer Research*, 62:5041-5048, 2002.
Su et al., "Immunological and Clinical Responses in Metastatic Renal Cancer Patients Vaccinated with Tumor RNA-transfected Dendritic Cells," *Cancer Research*, 63:2127-2133, 2003.
Suda et al., "Hydrodynamic gene delivery: its principles and applications," *Mol. Ther.*, 15(12):2063-2069, 2007.
Sullenger et al., "Emerging clinical applications of RNA," *Nature*, 418(6894):252-258, 2002.
Svinarchuk et al., "Inhibition of HIV proliferation in MT-4 cells by antisense oligonucleotide conjugated to lipophilic groups," *Biochimie*, 75(1-2):49-54, 1993.
Tang et al., "Genetic immunization is a simple method for eliciting an immune response," *Nature*, 356(6365):152-154, 1992.
Tazi and Bird, "Alternative chromatin structure at CpG islands," *Cell*, 60:909-920, 1990.
Teufel et al., "Human peripheral blood mononuclear cells transfected with messenger RNA stimulate antigen-specific cytotoxic T-lymphocytes in vitro," *Cell. Mol. Life Sci.*, 62:1755-1762, 2005.
Thurner et al., "Vaccination with mage-3A1 peptide-pulsed mature, monocyte-derived dendritic cells expands specific cytotoxic T cells and induces regression of some metastases in advanced stage IV melanoma," *J Exp Med*, 190(11):1669-1678, 1999.
Tourriere et al., "mRNA degradation machines in eukaryotic cells," *Biochimie*, 84(8):821-837, 2002.

Trinchieri et al., "Cooperation of Toll-like receptor signals in innate immune defence," *Nature Reviews Immunology*, 7:179-190, 2007.
Trojan et al., "Immune reactivity against a novel HLA-A3-restricted influenza virus peptide identified by predicative algorithms and interferon-gamma quantitative PCR," *Journal of Immunotherapy*, 26(1):41-46, 2003.
Tüting et al., "Gene-based strategies for the immunotherapy of cancer," *J Mol Med*, 75:478-491, 1997.
Ueda et al., "Phosphorothioate-containing RNAs show mRNA activity in the prokaryotic translation systems in vitro," *Nucleic Acids Res.*, 19(3):547-552, 1991.
Ulmer et al., "Heterologous protection against influenza by injection of DNA encoding a viral protein," *Science*, 259(5102):1745-1749, 1993.
Ulmer, "An update on the state of the art of DNA vaccines," *Curr Opin Drug Discov Devel*, 4(2):192-197, 2001.
Vassilev et al., "Microparticle-mediated RNA immunization against bovine viral diarrhea virus," *Vaccine*, 19(15-1 6):2012-2019, 2001.
Verma et al., "Gene therapy—promises, problems and prospects," *Nature*, 389(6648):239-242, 1997.
Verma er al., "Gene therapy: twenty-first century medicine," *Annu. Rev. Biochem.*, 74:711-738, 2005.
Villaret et al., "Identification of genes overexpressed in head and neck squamous cell carcinoma using a combination of complementary DNA subtraction and microarray analysts," *The Laryngoscope*, 110: 374-381, 2000.
Wang et al., "Gene inoculation generates immune responses against human immunodeficiency virus type 1," *Proc Natl Acad Sci USA*, 90(9):4156-4160, 1993.
Warren et al., "Uses of granulocyte-macrophage colony-stimulating factor in vaccine development," *Curr Opin Hematol*, 7(3):168-173, 2000.
Watanabe et al., "Induction of wild-type p53 activity in human cancer cells by ribozymes that repair mutant p53 transcripts," *PNAS*, 97(15):8490-8494, 2000.
Weber et al., "Granulocyte-macrophage-colony-stimulating factor added to a multipeptide vaccine for resected Stage II melanoma," *Cancer*, 97(1):186-200, 2003.
Weide et al., "Results of the First Phase I/II Clinical Vaccination Trial with Direct Injection of mRNA," *J. Immunother.*, 31(2):180-188, 2008.
Weissman et al., "HIV gag mRNA transfection of dendritic cells (DC) delivers encoded antigen to MHC class I and II molecules, causes DC maturation, and induces a potent human in vitro primary immune response," *J. Immunol.*, 165(8):4710-4717, 2000.
Weissmann el al., "Dendritic cells express and use multiple HIV coreceptors," *Adv Exp Med Biol*, 417:401-406, 1997.
Wikipedia Diagram, "A peripheral blood mononuclear cell," 2011.
Wilusz el al., "Bringing the role of mRNA decay in the control of gene expression into focus," *Trends Genet.*, 20(10):491-497, 2004.
Wolff et al., "Direct gene transfer into mouse muscle in vivo," *Science*, 247(4949 Pt. 1):1465-1468, 1990.
Woodberry et al., "Immunogenicity of a human immunodeficiency virus (HIV) polytope vaccine containing multiple HLA A2 HIV CD8(+) cytotoxic T-cells epitopes," *Journal of Virology*, 73(7):5320-5325, 1999.
Wu et al., "Fusion protein vectors to increase protein production and evaluate the immunogenicity of genetic vaccines," *Mol. Ther.*, 2(3):288-297, 2000.
Xu et al., "Identification of differentially expressed genes in human prostate cancer using subtraction and microarray," *Cancer Research*, 60:1677-1682. 2000.
Ying et al., "Cancer therapy using a self-replicating RNA vaccine," *Nat Med.* 5(7):823-827, 1999.
You et al., "A retrogen strategy for presentation of an intracellular tumor antigen as an exogenous antigen by dendritic cells induces potent antitumor T helper and CTL responses," *Cancer Research*, 61:197-205, 2001.
Zhang et al., "Advances in dendritic cell-based vaccine of cancer," *Cancer Biotherapy & Radiopharmaceuticals*, 17:601-619, 2002.
Zhou et al., "Papillomavirus capsid protein expression level depends on the match between codon usage and tRNA availability," *Journal of Virology*, 73(6):4972-4982, 1999.

(56) References Cited

OTHER PUBLICATIONS

Zhou et al., "RNA melanoma vaccine: induction of antitumor immunity by human glycoprotein 100 mRNA immunization," *Human Gene Therapy*, 10:2719-2724, 1999.
Zitvogel et al., "Therapy of murine tumors with tumor peptide-pulsed dendritic cells: dependence on T cells, B7 costimulation, and T helper cell 1-associated cytokins," *J Exp Med*, 183(1):87-97, 1996.
Zrihan-Licht et al., "Characterization and molecular cloning of a novel MUC1 protein devoid of tandem repeats, expressed in human breast cancer tissue," *European Journal of Biochemistry*, 224:787-795, 1994.
Deml et al., "Multiple effects of codon usage optimization on expression and immunogenicity of DNA candidate vaccines encoding the human immunodeficiency virus type 1 Gag protein," *Journal of Virology*, 75(22):10991-11001, 2001.
George and Raju, "Alphavirus RNA genome repair and evolution: molecular characterization of infectious Sindbis virus isolates lacking a known conserved motif at the 3' end of the genome," *Journal of Virology*, 74(20):9776-9785, 2000.
Mauro et al., "A critical analysis of codon optimization in human therapeutics," *Trends in Molecular Medicine*, 20(11):604-613, 2014.
Office Action issued in U.S. Appl. No. 15/005,911, dated Mar. 9, 2021.
Pardi et al., "mRNA vaccines—a new era in vaccinology," *Nature Reviews*, 17(4):261-279, 2018.
Pascolo, "Messenger RNA-based vaccines," *Expert Opinion on Biological Therapy*, 4(8):1285-1294, 2004.
Raju er al., "In vivo addition of poly(A) tail and AU-rich sequences to the 3' terminus of the Sindbis virus RNA genome: a novel 3'-end repair pathway," *Journal of Virology*, 73(3):241-2419, 1999.
Bowie et al., "Deciphering the message in protein sequences: tolerance to amino acid substitutions," Science, 247:1306-1310, 1990.
Certified Translation of German Application No. DE 101 27 283.9, filed Jun. 5, 2001, Certification dated Nov. 27, 2019.
Cold Spring Harbor Protocols, "Phosphate buffered saline (PBS)." Recipe. 2006.
Decision by Patent Trial and Appeal Board issued in U.S. Appl. No. 10/729,830, dated Jun. 25, 2018.
Declaration of Dr. Ingmar Hoerr Under 37 C.F.R. § 1.132 submitted in U.S. Appl. No. 10/729,830, filed Oct. 14, 2008.
Declaration of Dr. Ingmar Hoerr Under 37 C.F.R. § 1.132 submitted in U.S. Appl. No. 10/729,830, filed Dec. 22, 2009.
Declaration of Marshall Byrd Under 37 C.F.R. § 1.132 submitted in U.S. Appl. No. 10/729,830, filed Dec. 15, 2014.
Declaration Under 37 C.F.R. § 1.132 of Dr. Benjamin Petsch, submitted in U.S. Appl. No. 14/994,913 dated Sep. 17, 2018.
Declaration Under 37 C.F.R. § 1.132 of Benjamin Petsch for U.S. Appl. No. 15/005,863, submitted Nov. 27, 2018.
Dowdy, "Overcoming cellular barriers for RNA therapeutics," Nature Biotechnology, 35:222-220, 2017.
Ellis et al., "Ebola virus: a comparison, at ultrastructural level, of the behaviour of the Sudan and Zaire strains in monkeys," British Journal of Experimental Pathology, 59:584-593, 1978.
Fleeton et al., "Self-replicative RNA vaccines elicit protection against influenza A virus, respiratory syncytial virus, and a tickborne encephalitis virus," J. Infect. Dis., 183:1395-8, 2001.
Frolov & Schlesinger, "Translation of Sindbis virus mRNA: analysis of sequences downstream of the initiating AUG codon that enhance translation," J. Virol., 70:1182-1190, 1996.
Gilboa, "The promise of cancer vaccines," Nature Reviews Cancer, 4:401-411, 2004.
Graf et al., "Concerted action of multiple cis-acting sequences is required for Rev dependent of late human immunodeficiency virus type 1 gene expression," Journal of Virology, 74:10822-10826, 2000.
Greenspan et al., "Defining epitopes: It's not as easy as it seems," Nat. Biotechnol., 17:936-937, 1999.
Griesenbach et al., "Gene transfer to the lung: Lessons learned from more than 2 decades of CF gene therapy," Advanced Drug Delivery Reviews, 61:128-139, 2009.
Gustafsson et al., "Codon bias and heterologous protein expression", 2001.
Kowalski et al., "Delivering the messenger: Advances in technologies for therapeutic mRNA delivery," Mol. Ther., 27:710-728, 2019.
Lai et al., "Patterning of the neural ectoderm of Xenopus laevis by the amino-terminal product of hedgehog autoproteolytic cleavage," Development, 121(8):2349-2360, 1995.
Lakey et al., "Enhanced production of recombinant Mycobacterium tuberculosis antigens in *Escherichia coli* by replacement of low-usage codons," Infect. Immun., 68:233-238, 2000.
Lutz et al., "Unmodified mRNA in LNPs constitutes a competitive technology for prophylactic vaccines," NPJ Vaccines, 2:29, 2017.
Mandi et al., "In vitro-synthesized infectious RNA as an attenuated live vaccine in a flavivirus model," Nat. Med., 4:1438-1440, 1998.
Mateu et al., "Non-additive effects of multiple amino acid substitutions on antigenantibody recognition," Eur. J. Immunol., 22:1385-1389, 1992.
Megede et al., "Increased expression and immunogenicity of sequence-modified human immunodeficiency virus type 1 gag gene," J. Virol., 74:2628-2635, 2000.
Murphy et al., "A combinatorial approach to the discovery of efficient cationic peptoid reagents for gene delivery," PNAS, 95:1517-1522, 1998.
NCBI Accession No. NM_000378, 2014.
NCBI Accession No. NM_001648, 2014.
Office Action issued in U.S. Appl. No. 10/729,830, dated Jun. 25, 2018.
Office Action issued in U.S. Appl. No. 10/729,830, dated May 15, 2009.
Office Action issued in U.S. Appl. No. 10/729,830, dated Mar. 3, 2015.
Office Action issued in U.S. Appl. No. 10/729,830, dated Sep. 20, 2011.
Office Action issued in U.S. Appl. No. 13/361,686, dated Aug. 7, 2013.
Office Action issued in U.S. Appl. No. 13/361,686, dated Dec. 29, 2014.
Office Action issued in U.S. Appl. No. 13/361,686, dated Feb. 27, 2014.
Office Action issued in U.S. Appl. No. 13/361,686, dated Nov. 13, 2014.
Office Action issued in U.S. Appl. No. 13/361,686, dated Oct. 24, 2012.
Office Action issued in U.S. Appl. No. 14/487,425, dated Apr. 14, 2017.
Office Action issued in U.S. Appl. No. 14/487,425, dated Aug. 10, 2018.
Office Action issued in U.S. Appl. No. 14/487,425, dated Apr. 9, 2020.
Office Action issued in U.S. Appl. No. 14/487,425, dated Jan. 26, 2018.
Office Action issued in U.S. Appl. No. 14/487,425, dated Jun. 22, 2020.
Office Action issued in U.S. Appl. No. 14/487,425, dated Sep. 23, 2016.
Office Action issued in U.S. Appl. No. 14/994,913, dated Dec. 18, 2018.
Office Action issued in U.S. Appl. No. 14/994,913, dated Feb. 6, 2020.
Office Action issued in U.S. Appl. No. 14/994,913, dated Jul. 10, 2019.
Office Action issued in U.S. Appl. No. 14/994,913, dated Mar. 16, 2018.
Office Action issued in U.S. Appl. No. 14/994,913, dated Sep. 10, 2021.
Office Action issued in U.S. Appl. No. 15/005,753, dated Apr. 23, 2018.
Office Action issued in U.S. Appl. No. 15/005,863, dated Feb. 26, 2019.

(56) References Cited

OTHER PUBLICATIONS

Office Action issued in U.S. Appl. No. 15/005,863, dated May 16, 2018.
Office Action issued in U.S. Appl. No. 15/005,911, dated Apr. 26, 2019.
Office Action issued in U.S. Appl. No. 15/005,911, dated Jun. 5, 2020.
Office Action issued in U.S. Appl. No. 15/005,911, dated Mar. 15, 2018.
Office Action issued in U.S. Appl. No. 15/005,911, dated Nov. 5, 2018.
Office Action issued in U.S. Appl. No. 15/005,911, dated Dec. 29, 2021.
Office Action issued in U.S. Appl. No. 15/005,950, dated Apr. 10, 2018.
Office Action issued in U.S. Appl. No. 15/005,950, dated Mar. 5, 2019.
Office Action issued in U.S. Appl. No. 15/206,488, dated Jun. 16, 2017.
Office Action issued in U.S. Appl. No. 16/116,320, dated Feb. 25, 2021.
Office Action issued in U.S. Appl. No. 16/116,320, dated Nov. 2, 2021.
Office Action issued in U.S. Appl. No. 16/116,320, dated Oct. 28, 2021.
Petsch et al., "Protective efficacy of in vitro synthesized, specific mRNA vaccines against influenza A virus infection," Nature Biotechnology, 30(12):1210-1218, 2012.
Pollard et al., "Type I IFN counteracts the induction of antigen-specific immune responses by lipid-based delivery of mRNA vaccines," Molecular Therapy, 21(1):251-259, 2013.
Rathore, "Cross-reactive immunity among flaviviruses," Front. Immunol., 11:334, 2020.
Rauch et al., "mRNA based SARS-CoV-2 vaccine candidate CVnCoV induces high levels of virus neutralizing antibodies and mediates protection in rodents," bioRxiv preprint, Feb. 9, 2021.
Rauch et al., "mRNA vaccine CVnCoV protects non-human primates from SARS-CoV-2 challenge infection," bioRxiv preprint, Dec. 23, 2020.
Rauch et al., "New vaccine technologies to combat outbreak situations," Frontiers in Immunology, 9:1963, 2018.
Rice, "Examples of expression systems based on animal RNA viruses: alphaviruses and influenza virus," Curr. Opin. Biotechnol., 3:523-32, 1992.
Richner et al., "Modified mRNA vaccines protect against Zika virus infection," Cell, 168:1114-1125, 2017.
Richner et al., "Vaccine mediated protection against Zika virus induced congenital disease," Cell, 170:273-283, 2017.
Sahin et al., "mRNA-based therapeutics—developing a new class of drugs," Nat Rev Drug Discov., 13(10):759-780, 2014.
Sirin et al., "AB-Bind: Antibody binding mutational database for computational affinity predictions," Protein Sci., 25:393-409, 2016. Epub Nov. 6, 2015.
Srinivasan and Wolchok, "Tumor antigens for cancer immunotherapy: therapeutic potential of xenogeneic DNA vaccines," Journal of Translational Medicine, 2:12, 2004.
Taylor, Translate Bio's mRNA fails to improve lung function in cystic fibrosis patients, https://www.fiercebiotech.com/biotech/translate-bio-s-mrna-fails-to-improve-lung-function-cystic-fibrosis-patients, 2021.
Tripathy et al., "Long-term expression of erythropoietin in the systemic circulation of mice after intramuscular injection of a plasmid DNA vector," PNAS, 93:10876-10880, 1996.
Vanblargan et al., "An mRNA vaccine protects mice against multiple tick-transmitted Flavivirus infections," Cell Rep., 25:3382-3392, 2018.
Vanderzanden et al., "DNA vaccines expressing either the GP or NP genes of Ebola virus protect mice from lethal challenge," Virology, 246:134-144, 1998.
Volchkov et al., "GP mRNA of Ebola virus is edited by the Ebola virus polymerase and by T7 and vaccinia virus polymerases," Virology, 214:421-430, 1995.
Winkler et al., "Changing the antigen binding specificity by single point mutations of an anti-p24 (HIV-1) antibody," J. Immunol., 165:4505-4514, 2000.
Zambon, "Epidemiology and pathogenesis of influenza," Journal of Antimicrobial Chemotherapy, 44 Suppl B:3-9, 1999.
Australian Provisional Application No. PR 4468, filed Apr. 18, 2001.
Office Action issued in U.S. Appl. No. 14/994,913, dated Feb. 9, 2022.

\* cited by examiner

Fig. 1A

Influenza matrix: wild type gene (for comparison)

agatctaaagatgagtcttctaaccgaggtcgaaacgtacgttctctcta
tcatcccgtcaggccccctcaaagccgagatcgcacagagacttgaagat
gtctttgcagggaagaacaccgatcttgaggttctcatggaatggctaaa
gacaagaccaatcctgtcacctctgactaaggggattttaggatttgtgt
tcacgctcaccgtgcccagtgagcgaggactgcagcgtagacgctttgtc
caaaatgcccttaatgggaacggggatccaaataacatggacaaagcagt
taaactgtataggaagctcaagagggagataacattccatggggccaaag
aaatctcactcagttattctgctggtgcacttgccagttgtatgggcctc
atatacaacaggatgggggctgtgaccactgaagtggcatttggcctggt
atgtgcaacctgtgaacagattgctgactcccagcatcggtctcataggc
aaatggtgacaacaaccaacccactaatcagacatgagaacagaatggtt
ttagccagcactacagctaaggctatggagcaaatggctggatcgagtga
gcaagcagcagaggccatggaggttgctagtcaggctaggcaaatggtgc
aagcgatgagaaccattgggactcatcctagctccagtgctggtctgaaa
aatgatcttcttgaaaatttgcaggcctatcagaaacgaatgggggtgca
gatgcaacggttcaagtgaactag

Fig. 1B

Influenza matrix: protein sequence

MSLLTEVETYVLSIIPSGPLKAEIAQRLEDVFAGKNTDLEVLMEWLKTRP
ILSPLTKGILGFVFTLTVPSERGLQRRRFVQNALNGNGDPNNMDKAVKLY
RKLKREITFHGAKEISLSYSAGALASCMGLIYNRMGAVTTEVAFGLVCAT
CEQIADSQHRSHRQMVTTTNPLIRHENRMVLASTTAKAMEQMAGSSEQAA
EAMEVASQARQMVQAMRTIGTHPSSSAGLKNDLLENLQAYQKRMGVQMQR
FK*

Fig. 1C

Influenza matrix: gene with increased G/C content agatctaaagatgagCctGctGaccgaggtGgaGacCtacgtGctGAGCa
tcatcccCAGCggcccccctGaaGgccgagatcgcCcagagGctGgaGgaC
gtGttCgcCggCaagaacaccgaCctGgaggtGctGatggaGtggctGaa
gacCagGccCatcctgAGCccCctgacCaagggCatCCTGggCttCgtgt
tcacCctGaccgtgcccagCgagcgCggCctgcagcgCCGCcgcttCgtG
caGaaCgccctGaaCggCaacggCgaCccCaaCaacatggacaaGgcCgt
GaaGctgtaCaggaagctGaagagggagatCacCttccaCggCgccaaGg
aGatcAGCctGagCtaCAGCgcCggCgcCctGgccagCtgCatgggcctG
atCtacaacaggatgggCgcCgtgaccacCgaGgtggcCttCggcctggt
GtgCgcCacctgCgaGcagatCgcCgacAGCcagcaCcgCAGCcaCaggc
aGatggtgacCacCaccaacccCctGatcagGcaCgagaacagGatggtG
CTGgccagcacCacCgcCaaggcCatggagcaGatggcCggCAGCaGCga
gcaGgcCgcCgaggccatggaggtGgcCagCcaggcCaggcaGatggtgc
aGgcCatgagGaccatCggCacCcaCccCagcAGCagCgcCggCctgaaG
aaCgaCctGctGgaGaaCCTGcaggcctaCcagaaGcgCatgggCgtgca
gatgcaGcgCttcaagtgaactagt

Fig. 1D

Influenza matrix: gene for secreted form (with N-terminal
signal sequence) with increased G/C content AgatctaaagatgGCCGTCATGGCCCCCCGCACCCTGGTGCTGCTGCTGA
GCGGCGCCCTGGCCCTGACCCAGACCTGGGCTagCctGctGaccgaggtG
gaGacCtacgtGctGAGCatcatcccCAGCggcccccctGaaGgccgagat
cgcCcagagGctGgaGgaCgtGttCgcCggCaagaacaccgaCctGgagg
tGctGatggaGtggctGaagacCagGccCatcctgAGCccCctgacCaag
ggCatCCTGggCttCgtgttcacCctGaccgtgcccagCgagcgCggCct
gcagcgCCGCcgcttCgtGcaGaaCgccctGaaCggCaacggCgaCccCa
aCaacatggacaaGgcCgtGaaGctgtaCaggaagctGaagagggagatC
acCttccaCggCgccaaGgaGatcAGCctGagCtaCAGCgcCggCgcCct
GgccagCtgCatgggcctGatCtacaacaggatgggCgcCgtgaccacCg
aGgtggcCttCggcctggtGtgCgcCacctgCgaGcagatCgcCgacAGC
cagcaCcgCAGCcaCaggcaGatggtgacCacCaccaacccCctGatcag
GcaCgagaacagGatggtGCTGgccagcacCacCgcCaaggcCatggagc
aGatggcCggCAGCaGCgagcaGgcCgcCgaggccatggaggtGgcCagC
caggcCaggcaGatggtgcaGgcCatgagGaccatCggCacCcaCccCag
cAGCagCgcCggCctgaaGaaCgaCctGctGgaGaaCCTGcaggcctaCc
agaaGcgCatgggCgtgcagatgcaGcgCttcaagtgaactagt

Fig. 1E

Influenza matrix: mRNA with stabilisation sequences

GCUUGUUCUUUUUGCAGAAGCUCAGAAUAAACGCUCAACUUUGGCagauc
uaaagaugagucuucuaaccgaggucgaaacgacguucucucuaucauc
ccgucaggcccccucaaagccgagaucgcacagagacuugaagaugucuu
ugcagggaagaacaccgaucuugagguucucauggaauggcuaaagacaa
gaccaauccugucaccucugacuaaggggauuuuaggauuuguguucacg
cucaccgugcccagugagcgaggacugcagcguagacgcuuuguccaaaa
ugcccuuaaugggaacggggauccaaauaacauggacaaagcaguuaaac
uguauaggaagcucaagagggagauaacauuccaugggggccaaagaaauc
ucacucaguuauucgcuggugcacuuccaguuuauggggccucauaua
caacaggauggggcugugaccacugaaguggcauuuggccugguaugug
caaccugugaacagauugcugacucccagcaucggucucauaggcaaaug
gugacaacaaccaacccacuaaucagacaugagaacagaaugguuuuagc
cagcacuacagcuaaggcuauggagcaaauggcuggaucgaguugagcaag
cagcagaggccauggagguugcuagucaggcuaggcaaauggugcaagcg
augagaaccauugggacucauccuagcuccagugcuggucugaaaaauga
ucuucuugaaaauuugcaggccaucagaaacgaauggggggugcagaugc
aacgguucaagugaACUAGUGACUGACUAGCCCGCUGGGCCUCCCAACGG
GCCCUCCUCCCCUCCUUGCACCAAAAAAAAAAAAAAAAAAAAAAAAAAAA
AAAAAAAAAAAAAAAAAAAAAAAAAAAAAAAAAAAAAAAAA

Fig. 1F

Influenza matrix: mRNA with increased G/C content and stabilisation sequences

GCUUGUUCUUUUUGCAGAAGCUCAGAAUAAACGCUCAACUUUGGCagauc
uaaagaugagCcuGcuGaccgagguGgaGacCuacguGcuGAGCaucauc
ccCAGCggccccuGaaGgccgagaucgcCcagagGcuGgaGgaCguGuu
CgcCggCaagaacaccgaCCuGgagguGcuGauggaGuggcuGaagacCa
gGccCauccugAGCccCcugacCaagggCauCCUGggCuuCguguucacC
cuGaccgugcccagCgagcgCggCcugcagcgCCGCcgcuuCguGcaGaa
CgcccuGaaCggCaacggCgaCccCaaCaacauggacaaGgcCguGaaGc
uguaCaggaagcuGaagagggagauCacCuuccaCggCgccaaGgaGauc
AGCcuGagCuaCAGCgcCggCgcCcuGgccagCugCaugggccuGauCua
caacaggauggGCgcCgugaccacCgaGguggcCuuCggccugguGugCg
cCaccugCgaGcagauCgcCgacAGCcagcaCcgCAGCcaCaggcaGaug
gugacCacCaccaaccCCcuGaucagGcaCgagaacagGaugguGCUGgc
cagcacCacCgcCaaggcCauggagcaGauggCggCAGCaGCgagcaGg
cCgcCgaggccauggagguGgcCagCcaggcCaggcaGauggugcaGgcC
augagGaccauCggCacCcaCccCagcAGCagCgcCggCcugaaGaaCga
CcuGcuGgaGaaCCUGcaggccuaCcagaaGcgCaugggCgugcagaugc
aGcgCuucaagugaACUAGUGACUGACUAGCCCGCUGGGCCUCCCAACGG
GCCCUCCUCCCCUCCUUGCACCAAAAAAAAAAAAAAAAAAAAAAAAAAAA
AAAAAAAAAAAAAAAAAAAAAAAAAAAAAAAAAAAAAAAA

Fig. 1G

Influenza matrix: mRNA coding for secreted form with increased G/C content and stabilisation sequences GCUUGUUCUUUUUGCAGAAGCUCAGAAUAAACGCUCAACUUUGGCagauc
uaaagaugGCCGUCAUGGCCCCCCGCACCCUGGUGCUGCUGCUGAGCGGC
GCCCUGGCCCUGACCCAGACCUGGGCCagCcuGcuGaccgagguGgaGac
CuacguGcuGAGCaucaucccCAGCggcccccuGaaGgccgagaucgcCc
agagGcuGgaGgaCguGuuCgcCggCaagaacaccgaCcuGgagguGcuG
auggaGuggcuGaagacCagGccCauccugAGCccCcugacCaagggCau
CCUGggCuuCguguucaCCcuGaccgugcccagCgagcgCggCcugcagc
gCCGCcgcuuCguGcaGaaCgcccuGaaCggCaacggCgaCccCaaCaac
auggacaaGgcCguGaaGcuguaCaggaagcuGaagagggagauCacCuu
ccaCggCgccaaGgaGaucAGCcuGagCuaCAGCgcCggCgcCcuGgcca
gCugCaugggccuGauCuacaacaggaugggCgcCgugaccacCgaGgug
gcCuuCggccugguGugCgcCaccugCgaGcagauCgcCgacAGCcagca
CcgCAGCcaCaggcaGauggugacCacCaccaacccCcuGaucagGcaCg
agaacagGauggUGCUGgccagcacCacCgcCaaggcCauggagcaGaug
gcCggCAGCaGCgagcaGgcCgcCgaggccauggagguGgcCagCcaggc
CaggcaGauggugcaGgcCaugagGaccauCggCacCcaCccCagcAGCa
gCgcCggCcugaaGaaCgaCcuGcuGgaGaaCCUGcaggccuaCcagaaG
cgCaugggCgugcagaugcaGcgCuucaagugaACUAGUGACUGACUAGC
CCGCUGGGCCUCCCAACGGGCCCUCCUCCCCUCCUUGCACCAAAAAAAAA
AAAAAAAAAAAAAAAAAAAAAAAAAAAAAAAAAAAAAAAAAAAAAAAAA
AAAAAAAAAA

Fig. 2A

MAGE1: wild type gene (for comparison)

catcatgtctcttgagcagaggagtctgcactgcaagcctgaggaagccc
ttgaggcccaacaagaggccctgggcctggtgtgtgtgcaggctgccacc
tcctcctcctctcctctggtcctgggcacctggaggaggtgcccactgc
tgggtcaacagatcctccccagagtcctcagggagcctccgccttccca
ctaccatcaacttcactcgacagaggcaacccagtgagggttccagcagc
cgtgaagaggaggggccaagcacctcttgtatcctggagtccttgttccg
agcagtaatcactaagaaggtggctgatttggttggttttctgctcctca
aatatcgagccagggagccagtcacaaggcagaaatgctggagagtgtc
atcaaaaattacaagcactgttttcctgagatcttcggcaaagcctctga
gtccttgcagctggtctttggcattgacgtgaaggaagcagaccccaccg
gccactcctatgtccttgtcacctgcctaggtctctcctatgatggcctg
ctgggtgataatcagatcatgcccaagacaggcttcctgataattgtcct
ggtcatgattgcaatggagggcggccatgctcctgaggagaaatctggg
aggagctgagtgtgatggaggtgtatgatgggagggagcacagtgcctat
ggggagcccaggaagctgctcacccaagatttggtgcaggaaaagtacct
ggagtaccggcaggtgccggacagtgatcccgcacgctatgagttcctgt
ggggtccaagggccctcgctgaaaccagctatgtgaaagtccttgagtat
gtgatcaaggtcagtgcaagagttcgcttttcttcccatccctgcgtga
agcagctttgagagaggaggaagagggagtctgagcatga

Fig. 2B

MAGE1: protein sequence

SER,LEU,GLU,GLN,ARG,SER,LEU,HIS,CYS,LYS,PRO,GLU,GLU,ALA,LEU,GL
U,ALA,GLN,GLN,GLU,ALA,LEU,GLY,LEU,VAL,CYS,VAL,GLN,ALA,ALA,THR,
SER,SER,SER,SER,PRO,LEU,VAL,LEU,GLY,THR,LEU,GLU,GLU,VAL,PRO,TH
R,ALA,GLY,SER,THR,ASP,PRO,PRO,GLN,SER,PRO,GLN,GLY,ALA,SER,ALA,
PHE,PRO,THR,THR,ILE,ASN,PHE,THR,ARG,GLN,ARG,GLN,PRO,SER,GLU,GL
Y,SER,SER,SER,ARG,GLU,GLU,GLU,GLY,PRO,SER,THR,SER,CYS,ILE,LEU,
GLU,SER,LEU,PHE,ARG,ALA,VAL,ILE,THR,LYS,LYS,VAL,ALA,ASP,LEU,VA
L,GLY,PHE,LEU,LEU,LEU,LYS,TYR,ARG,ALA,ARG,GLU,PRO,VAL,THR,LYS,
ALA,GLU,MET,LEU,GLU,SER,VAL,ILE,LYS,ASN,TYR,LYS,HIS,CYS,PHE,PR
O,GLU,ILE,PHE,GLY,LYS,ALA,SER,GLU,SER,LEU,GLN,LEU,VAL,PHE,GLY,
ILE,ASP,VAL,LYS,GLU,ALA,ASP,PRO,THR,GLY,HIS,SER,TYR,VAL,LEU,VA
L,THR,CYS,LEU,GLY,LEU,SER,TYR,ASP,GLY,LEU,LEU,GLY,ASP,ASN,GLN,
ILE,MET,PRO,LYS,THR,GLY,PHE,LEU,ILE,ILE,VAL,LEU,VAL,MET,ILE,AL
A,MET,GLU,GLY,GLY,HIS,ALA,PRO,GLU,GLU,GLU,ILE,TRP,GLU,GLU,LEU,
SER,VAL,MET,GLU,VAL,TYR,ASP,GLY,ARG,GLU,HIS,SER,ALA,TYR,GLY,GL
U,PRO,ARG,LYS,LEU,LEU,THR,GLN,ASP,LEU,VAL,GLN,GLU,LYS,TYR,LEU,
GLU,TYR,ARG,GLN,VAL,PRO,ASP,SER,ASP,PRO,ALA,ARG,TYR,GLU,PHE,LE
U,TRP,GLY,PRO,ARG,ALA,LEU,ALA,GLU,THR,SER,TYR,VAL,LYS,VAL,LEU,
GLU,TYR,VAL,ILE,LYS,VAL,SER,ALA,ARG,VAL,ARG,PHE,PHE,PHE,PRO,SE
R,LEU,ARG,GLU,ALA,ALA,LEU,ARG,GLU,GLU,GLU,GLU,GLY,VAL,STP -
,ALA,STP

Fig. 2C

MAGE1: mRNA with increased G/C content augagccuggagcagcgcagccugcacugcaagccggaggaggcgcuggaggcgcagcagga
ggcgcugggccuggucugcguccaggcggcgacgagcagcagcagcccgcugguccugggca
cgcuggaggaggucccgacggcgggcagcacggacccgccgcagagcccgcagggcgcgagc
gcguucccgacgacgaucaacuucacgcgccagcgccagccgagcgagggcagcagcagccg
cgaggaggagggccccgagcacgagcugcauccuggagagccuguuccgcgcggucaucacga
agaaggucgcggaccuggucggcuuccugcugcugaaguaccgcgcgcgcgagccggucacg
aaggcggagaugcuggagagcgucaucaagaacuacaagcacugcuucccggagaucuucgg
caaggcgagcgagagccugcagcuggucuucggcaucgacgucaaggaggcggacccgacgg
gccacagcuacguccuggucacgugccugggccugagcuacgacggccugcugggcgacaac
cagaucaugccgaagacgggcuuccugaucaucguccuggucaugaucgcgauggagggcgg
ccacgcgccggaggaggagaucugggaggagcugagcgucauggaggucuacgacggccgcg
agcacagcgcguacggcgagccgcgcaagcugcugacgcaggaccugguccaggagaaguac
cuggaguaccgccaggucccggacagcgacccggcgcgcuacgaguuccuguggggcccgcg
cgcgcuggcggagacgagcuacgucaagguccuggaguacgucaucaaggucagcgcgcgcg
uccgcuucuucuucccgagccugcgcgaggcggcgcugcgcgaggaggaggagggcgucuga
gcgugauga

Fig. 2D

MAGE1: mRNA with alternative codon usage augagccuggagcagcgcagccugcacugcaagcccgaggaggcccuggaggcccagcagga
ggcccugggccuggugugcgugcaggccgccaccagcagcagcagcccccuggugcugggca
cccuggaggaggugcccaccgccggcagcaccgaccccccagagcccccagggcgccagc
gccuucccaccaccaucaacuucacccgccagcgccagcccagcgagggcagcagcagccg
cgaggaggagggccccagcaccagcugcauccuggagagccuguuccgcgccgugaucacca
agaaggugccgaccuggugggcuuccugcugcugaaguaccgcgcccgcgagcccgugacc
aaggccgagaugcuggagagcgugaucaagaacuacaagcacugcuucccgagaucuucgg
caaggccagcgagagccugcagcuggucuucggcaucgacgugaaggaggccgacccaccg
gccacagcuacgugcuggugaccuqccugggccugagcuacgacggccugcugggcgacaac
cagaucaugcccaagaccggcuuccugaucaucgugcuggugaugaucgccauggagggcgg
ccacgccccgaggaggagaucugggaggagcugagcgugauggagguguacgacggccgcg
agcacagcgccuacggcgagccccgcaagcugcugacccaggaccuggugcaggagaaguac
cuggaguaccgccaggugcccgacagcgacccgcccgcuacgaguuccuguggggccccg
cgcccuggccgagaccagcuacgugaaggugcuggaguacgugaucaaggugagcgcccgcg
ugcgcuucuucuucccagccugcgcgaggccgcccugcgcgaggaggaggagggcguguga
gccugauga

SEQUENCE LISTING

```
<160> NUMBER OF SEQ ID NOS: 14

<210> SEQ ID NO 1
<211> LENGTH: 774
<212> TYPE: DNA
<213> ORGANISM: Influenza virus

<400> SEQUENCE: 1
agatctaaag atgagtcttc taaccgaggt cgaaacgtac gttctctcta tcatcccgtc     60
aggccccctc aaagccgaga tcgcacagag acttgaagat gtctttgcag ggaagaacac    120
cgatcttgag gttctcatgg aatggctaaa gacaagacca atcctgtcac ctctgactaa    180
ggggatttta ggatttgtgt tcacgctcac cgtgcccagt gagcgaggac tgcagcgtag    240
acgctttgtc caaaatgccc ttaatgggaa cggggatcca aataacatgg acaaagcagt    300
taaactgtat aggaagctca agagggagat aacattccat ggggccaaag aaatctcact    360
cagttattct gctggtgcac ttgccagttg tatgggcctc atatacaaca ggatgggggc    420
tgtgaccact gaagtggcat ttggcctggt atgtgcaacc tgtgaacaga ttgctgactc    480
ccagcatcgg tctcataggc aaatggtgac aacaaccaac ccactaatca gacatgagaa    540
cagaatggtt ttagccagca ctacagctaa ggctatggag caaatggctg gatcgagtga    600
gcaagcagca gaggccatgg aggttgctag tcaggctagg caaatggtgc aagcgatgag    660
aaccattggg actcatccta gctccagtgc tggtctgaaa aatgatcttc ttgaaaattt    720
gcaggcctat cagaaacgaa tgggggtgca gatgcaacgg ttcaagtgaa ctag          774

<210> SEQ ID NO 2
<211> LENGTH: 252
<212> TYPE: PRT
<213> ORGANISM: Influenza virus

<400> SEQUENCE: 2

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
```

```
            20                  25                  30
Ala Gly Lys Asn Thr Asp Leu Glu Val Leu Met Glu Trp Leu Lys Thr
            35                  40                  45

Arg Pro Ile Leu Ser Pro Leu Thr Lys Gly Ile Leu Gly Phe Val Phe
            50                  55                  60

Thr Leu Thr Val Pro Ser Glu Arg Gly Leu Gln Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
            130                 135                 140

Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
            195                 200                 205

Ala Arg Gln Met Val Gln Ala Met Arg Thr Ile Gly Thr His Pro Ser
            210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 3
<211> LENGTH: 775
<212> TYPE: DNA
<213> ORGANISM: Artificial Sequence
<220> FEATURE:
<223> OTHER INFORMATION: Synthetic oligonucleotide

<400> SEQUENCE: 3
agatctaaag atgagcctgc tgaccgaggt ggagacctac gtgctgagca tcatccccag      60
cggccccctg aaggccgaga tcgcccagag gctggaggac gtgttcgccg gcaagaacac     120
cgacctggag gtgctgatgg agtggctgaa gaccaggccc atcctgagcc ccctgaccaa     180
gggcatcctg ggcttcgtgt tcaccctgac cgtgcccagc gagcgcggcc tgcagcgccg     240
ccgcttcgtg cagaacgccc tgaacggcaa cggcgacccc aacaacatgg acaaggccgt     300
gaagctgtac aggaagctga agagggagat caccttccac ggcgccaagg agatcagcct     360
gagctacagc gccggcgccc tggccagctg catgggcctg atctacaaca ggatgggcgc     420
cgtgaccacc gaggtggcct tcggcctggt gtgcgccacc tgcgagcaga tcgccgacag     480
ccagcaccgc agccacaggc agatggtgac caccaccaac cccctgatca ggcacgagaa     540
caggatggtg ctggccagca ccaccgccaa ggccatggag cagatggccg gcagcagcga     600
gcaggccgcc gaggccatgg aggtggccag ccaggccagg cagatggtgc aggccatgag     660
gaccatcggc acccacccca gcagcagcgc cggcctgaag aacgacctgc tggagaacct     720
gcaggcctac cagaagcgca tgggcgtgca gatgcagcgc ttcaagtgaa ctagt         775
```

<210> SEQ ID NO 4
<211> LENGTH: 844
<212> TYPE: DNA
<213> ORGANISM: Artificial Sequence
<220> FEATURE:
<223> OTHER INFORMATION: Synthetic oligonucleotide

<400> SEQUENCE: 4

```
agatctaaag atggccgtca tggccccccg caccctggtg ctgctgctga gcggcgccct      60
ggccctgacc cagacctggg ctagcctgct gaccgaggtg gagacctacg tgctgagcat     120
catccccagc ggcccctga aggccgagat cgcccagagg ctggaggacg tgttcgccgg     180
caagaacacc gacctggagg tgctgatgga gtggctgaag accaggccca tcctgagccc     240
cctgaccaag gcatcctgg gcttcgtgtt caccctgacc gtgcccagcg agcgcggcct     300
gcagcgccgc cgcttcgtgc agaacgccct gaacggcaac ggcgacccca caacatggga     360
caaggccgtg aagctgtaca ggaagctgaa gagggagatc accttccacg cgccaaggac      420
gatcagcctg agctacagcg ccggcgccct ggccagctgc atgggcctga tctacaacag     480
gatgggcgcc gtgaccaccg aggtggcctt cggcctggtg tgcgccacct gcgagcagat     540
cgccgacagc cagcaccgca gccacaggca gatggtgacc accaccaacc ccctgatcag     600
gcacgagaac aggatggtgc tggccagcac caccgccaag gccatggagc agatggccgg     660
cagcagcgag caggccgccg aggccatgga ggtggccagc caggccaggc agatggtgca     720
ggccatgagg accatcggca cccacccccag cagcagcgcc ggcctgaaga cgacctgct     780
ggagaacctg caggcctacc agaagcgcat gggcgtgcag atgcagcgct tcaagtgaac     840
tagt                                                                 844
```

<210> SEQ ID NO 5
<211> LENGTH: 942
<212> TYPE: RNA
<213> ORGANISM: Artificial Sequence
<220> FEATURE:
<223> OTHER INFORMATION: Synthetic oligonucleotide

<400> SEQUENCE: 5

```
gcuuguucuu uuugcagaag cucagaauaa acgcucaacu uuggcagauc uaaagaugag      60
ucuucuaacc gaggucgaaa cguacguucu cucuaucauc ccgucaggcc cccucaaagc     120
cgagaucgca cagagacuug aagaugucuu ugcagggaag aacaccgauc uugagguucu     180
caauggaaugg cuaaagacaa gaccaauccu gucaccucug acuaagggga uuuuaggauu     240
uguguucacg cucaccgugc ccagugagcg aggacugcag cguagacgcu uguccaaaa     300
ugcccuuaau gggaacgggg auccaaauaa cauggacaaa gcaguuaaac uguauaggaa     360
gcucaagagg gagauaacau uccauggggc caaagaaauc ucacucaguu auucugcugg     420
ugcacuugcc aguuguaugg gccucauaua caacaggau gggcugug ccacugaagu       480
ggcauuuggc cugguaugug caaccuguga acagauugcu gacucccagc aucggcucua     540
uaggcaaaug ugacaacaa ccaacccacu aaucagacau gagaacagaa ugguuuuagc     600
cagcacuaca gcuaaggcua uggagcaaau ggcuggaucg agugagcaag cagcagaggc     660
caugggagguu gcuagucagg cuaggcaaau ggugcaagcg augagaacca uugggacuca     720
uccuagcucc agugcugguc ugaaaaauga ucuucuugaa aauuugcagg ccaucagaa     780
acgaaugggg gugcagaugc aacgguucaa gugaacuagu gacugacuag cccgcuggc     840
```

```
cucccaacgg gccuccuccc ccuccuugca ccaaaaaaaa aaaaaaaaaa aaaaaaaaaa    900
aaaaaaaaaa aaaaaaaaaa aaaaaaaaaa aaaaaaaaaa aa                      942

<210> SEQ ID NO 6
<211> LENGTH: 942
<212> TYPE: RNA
<213> ORGANISM: Artificial Sequence
<220> FEATURE:
<223> OTHER INFORMATION: Synthetic oligonucleotide

<400> SEQUENCE: 6
gcuuguucuu uuugcagaag cucagaauaa acgcucaacu uuggcagauc uaaagaugag     60
ccugcugacc gagguggaga ccuacgugcu gagcaucauc cccagcggcc cccugaaggc    120
cgagaucgcc cagaggcugg aggacguguu cgccggcaag aacaccgacc uggaggugcu    180
gauggagugg cugaagacca ggcccauccu gagcccccug accaagggca uccugggcuu    240
cguguucacc cugaccgugc ccagcgagcg cggccugcag cgccgccgcu ucgugcagaa    300
cgcccugaac ggcaacggcg accccaacaa cauggacaag gccgugaagc uguacaggaa    360
gcugaagagg gagaucaccu uccacggcgc caaggagauc agccugagcu acagcgccgg    420
cgcccuggcc agcugcaugg gccugaucua acaggaugg gcgccguga ccaccgaggu     480 ggccuucggc cuggugugcg ccaccugcga gcagaucgcc gacagccagc accgcagcca    540
caggcagaug gugaccacca caaccccccu gaucaggcac gagaacagga uggugcuggc    600
cagcaccacc gccaaggcca uggagcagau ggccggcagc agcgagcagg ccgccgaggc    660
caugggagug ccagccagg ccaggcagau ggugcaggcc augaggacca ucggcaccca    720
ccccagcagc agcgccggcc ugaagaacga ccugcuggag aaccugcagg ccuaccagaa    780
gcgcaugggc gugcagaugc agcgcuucaa gugaacuagu gacugacuag cccgcugggc    840
cucccaacgg gcccuccucc ccuccuugca ccaaaaaaaa aaaaaaaaaa aaaaaaaaaa    900
aaaaaaaaaa aaaaaaaaaa aaaaaaaaaa aaaaaaaaaa aa                      942

<210> SEQ ID NO 7
<211> LENGTH: 1011
<212> TYPE: RNA
<213> ORGANISM: Artificial Sequence
<220> FEATURE:
<223> OTHER INFORMATION: Synthetic oligonucleotide

<400> SEQUENCE: 7
gcuuguucuu uuugcagaag cucagaauaa acgcucaacu uuggcagauc uaaagauggc     60
cgucauggcc ccccgcaccc uggugcugcu gcugagcggc gcccuggccc ugacccagac    120
cugggccagc cugcugaccg agguggagac cuacgugcug agcaucaucc ccagcggccc    180
ccugaaggcc gagaucgccc agaggcugga ggacguguuc gccggcaaga acaccgaccu    240
ggaggugcug auggagugc ugaagaccag gcccauccug agcccccuga ccaagggcau    300
ccugggcuuc guguucaccc ugaccgugcc cagcgagcgc ggccugcagc gccgccgcuu    360
cgugcagaac gcccugaacg gcaacggcga ccccaacaac auggacaagg ccgugaagcu    420
guacaggaag cugaagaggg agaucaccuu ccacggcgcc aaggagauca gccugagcua    480
cagcgccggc gcccuggcca gcugcauggg ccugaucuac aacaggaugg gcgccgugac    540
caccgaggug gccuucggcc uggugugcgc caccugcgag cagaucgccg acagccagca    600
ccgcagccac aggcagaugg ugaccaccac caacccccug aucaggcacg agaacaggau    660
ggugcuggcc agcaccaccg ccaaggccau ggagcagaug gccggcagca gcgagcaggc    720
```

```
cgccgaggcc auggaggugg ccagccaggc caggcagaug gugcaggcca ugaggaccau    780
cggcacccac cccagcagca gcgccggccu gaagaacgac cugcuggaga accugcaggc    840
cuaccagaag cgcaugggcg ugcagaugca gcgcuucaag ugaacuagug acugacuagc    900
ccgcugggcc ucccaacggg cccuccuccc cuccuugcac caaaaaaaaa aaaaaaaaaa    960
aaaaaaaaaa aaaaaaaaaa aaaaaaaaaa aaaaaaaaaa aaaaaaaaaa a           1011

<210> SEQ ID NO 8
<211> LENGTH: 940
<212> TYPE: DNA
<213> ORGANISM: Homo sapiens

<400> SEQUENCE: 8
catcatgtct cttgagcaga ggagtctgca ctgcaagcct gaggaagccc ttgaggccca     60
acaagaggcc ctgggcctgg tgtgtgtgca ggctgccacc tcctcctcct ctcctctggt    120
cctgggcacc ctggaggagg tgcccactgc tgggtcaaca gatcctcccc agagtcctca    180
gggagcctcc gcctttccca ctaccatcaa cttcactcga cagaggcaac ccagtgaggg    240
ttccagcagc cgtgaagagg aggggccaag cacctcttgt atcctggagt ccttgttccg    300
agcagtaatc actaagaagg tggctgattt ggttggtttt ctgctcctca aatatcgagc    360
cagggagcca gtcacaaagg cagaaatgct ggagagtgtc atcaaaaatt acaagcactg    420
ttttcctgag atcttcggca aagcctctga gtccttgcag ctggtctttg gcattgacgt    480
gaaggaagca gaccccaccg gccactccta tgtccttgtc acctgcctag gtctctccta    540
tgatggcctg ctgggtgata atcagatcat gcccaagaca ggcttcctga taattgtcct    600
ggtcatgatt gcaatggagg gcggccatgc tcctgaggag gaaatctggg aggagctgag    660
tgtgatggag gtgtatgatg ggagggagca cagtgcctat ggggagccca ggaagctgct    720
cacccaagat ttggtgcagg aaaagtacct ggagtaccgg caggtgccgg acagtgatcc    780
cgcacgctat gagttcctgt ggggtccaag ggccctcgct gaaaccagct atgtgaaagt    840
ccttgagtat gtgatcaagg tcagtgcaag agttcgcttt ttcttcccat ccctgcgtga    900
agcagctttg agagaggagg aagagggagt ctgagcatga                          940

<210> SEQ ID NO 9
<211> LENGTH: 308
<212> TYPE: PRT
<213> ORGANISM: Homo sapiens

<400> SEQUENCE: 9

Ser Leu Glu Gln Arg Ser Leu His Cys Lys Pro Glu Glu Ala Leu Glu
1               5                   10                  15

Ala Gln Gln Glu Ala Leu Gly Leu Val Cys Val Gln Ala Ala Thr Ser
            20                  25                  30

Ser Ser Ser Pro Leu Val Leu Gly Thr Leu Glu Glu Val Pro Thr Ala
        35                  40                  45

Gly Ser Thr Asp Pro Pro Gln Ser Pro Gln Gly Ala Ser Ala Phe Pro
    50                  55                  60

Thr Thr Ile Asn Phe Thr Arg Gln Arg Gln Pro Ser Glu Gly Ser Ser
65                  70                  75                  80

Ser Arg Glu Glu Glu Gly Pro Ser Thr Ser Cys Ile Leu Glu Ser Leu
                85                  90                  95

Phe Arg Ala Val Ile Thr Lys Lys Val Ala Asp Leu Val Gly Phe Leu
            100                 105                 110
```

```
Leu Leu Lys Tyr Arg Ala Arg Glu Pro Val Thr Lys Ala Glu Met Leu
            115                 120                 125

Glu Ser Val Ile Lys Asn Tyr Lys His Cys Phe Pro Glu Ile Phe Gly
        130                 135                 140

Lys Ala Ser Glu Ser Leu Gln Leu Val Phe Gly Ile Asp Val Lys Glu
145                 150                 155                 160

Ala Asp Pro Thr Gly His Ser Tyr Val Leu Val Thr Cys Leu Gly Leu
                165                 170                 175

Ser Tyr Asp Gly Leu Leu Gly Asp Asn Gln Ile Met Pro Lys Thr Gly
            180                 185                 190

Phe Leu Ile Ile Val Leu Val Met Ile Ala Met Glu Gly Gly His Ala
        195                 200                 205

Pro Glu Glu Glu Ile Trp Glu Glu Leu Ser Val Met Glu Val Tyr Asp
    210                 215                 220

Gly Arg Glu His Ser Ala Tyr Gly Glu Pro Arg Lys Leu Leu Thr Gln
225                 230                 235                 240

Asp Leu Val Gln Glu Lys Tyr Leu Glu Tyr Arg Gln Val Pro Asp Ser
                245                 250                 255

Asp Pro Ala Arg Tyr Glu Phe Leu Trp Gly Pro Arg Ala Leu Ala Glu
            260                 265                 270

Thr Ser Tyr Val Lys Val Leu Glu Tyr Val Ile Lys Val Ser Ala Arg
        275                 280                 285

Val Arg Phe Phe Phe Pro Ser Leu Arg Glu Ala Ala Leu Arg Glu Glu
    290                 295                 300

Glu Glu Gly Val
305

<210> SEQ ID NO 10
<211> LENGTH: 939
<212> TYPE: RNA
<213> ORGANISM: Artificial Sequence
<220> FEATURE:
<223> OTHER INFORMATION: Synthetic oligonucleotide

<400> SEQUENCE: 10
augagccugg agcagcgcag ccugcacugc aagccggagg aggcgcugga ggcgcagcag     60
gaggcgcugg ccuggucug cguccaggcg gcgacgagca gcagcagccc gcugguccug    120
ggcacgcugg aggagguccc gacggcgggc agcacggacc cgccgcagag cccgcagggc    180
gcgagcgcgu ucccgacgac gaucaacuuc acgcgccagc gccagccgag cgagggcagc    240
agcagccgcg aggaggaggg cccgagcacg agcugcaucc uggagagccu guuccgcgcg    300
gucaucacga agaaggucgc ggaccugguc ggcuuccugc ugcugaagua ccgcgcgcgc    360
gagccgguca cgaaggcgga gaugcuggag agcgucauca gaacuacaa gcacugcuuc    420 ccggagaucu ucggcaaggc gagcgagagc cugcagcugg ucuucggcau cgacgucaag    480
gaggcggacc cgacgggcca cagcuacguc cuggucacgu gccugggccu gagcuacgac    540
ggccugcugg gcgacaacca gaucaugccg aagacgggcu uccugaucau cguccugguc    600
augaucgcga uggagggcgg ccacgcgccg gaggaggaga ucuggaggga gcugagcguc    660
auggaggucu acgacggccg cgagcacagc gcguacggcg agccgcgcaa gcugcugacg    720
caggaccugg uccaggagaa guaccuggag uaccgccagg ucccggacag cgacccggcg    780
cgcuacgagu uccugugggg cccgcgcgcg cuggcggaga cgagcuacgu caaggucug    840 gaguacguca ucaaggucag cgcgcgcguc cgcuucuucu ucccgagccu gcgcgaggcg    900
```

```
gcgcugcgcg aggaggagga gggcgucuga gcgugauga                                 939
```

<210> SEQ ID NO 11
<211> LENGTH: 939
<212> TYPE: RNA
<213> ORGANISM: Artificial Sequence
<220> FEATURE:
<223> OTHER INFORMATION: Synthetic oligonucleotide

<400> SEQUENCE: 11

```
augagccugg agcagcgcag ccugcacugc aagcccgagg aggcccugga ggcccagcag    60
gaggcccugg ccuggugug cgugcaggcc gccaccagca gcagcagccc ccuggugcug   120
ggcacccugg aggaggugcc caccgccggc agcaccgacc cccccagag ccccagggc    180
gccagcgccu uccccaccac caucaacuuc acccgccagc gccagcccag cgagggcagc   240
agcagccgcg aggaggaggg ccccagcacc agcugcaucc uggagagccu guuccgcgcc   300
gugaucacca agaaggugc cgaccuggug ggcuuccugc ugcugaagua ccgcgcccgc   360
gagcccguga ccaaggccga gaugcuggag agcgugauca agaacuacaa gcacugcuuc   420
cccgagaucu ucggcaaggc cagcgagagc cugcagcugg uguucggcau cgacgugaag   480
gaggccgacc ccaccggcca cagcuacgug cuggugaccu gccugggccu gagcuacgac   540
ggccugcugg cgacaaccca gaucaugccc aagaccggcu uccugaucau cgucugguc   600
augaucgcca uggagggcgg ccacgccccc gaggaggaga ucugggaga gcugagcgug   660
auggagugu acgacggccg cgagcacagc gccuacggcg agcccgcaa gcugcugacc   720
caggaccugg ugcaggagaa guaccuggag uaccgccagg ugcccgacag cgaccccgcc   780
cgcuacgagu uccugugggg cccccgcgcc cuggccgaga ccagcuacgu gaaggugcug   840
gaguacguga ucaaggugag cgcccgcgug cgcuucuucu uccccagccu gcgcgaggcc   900
gcccugcgcg aggaggagga gggcguguga gccugauga                            939
```

<210> SEQ ID NO 12

<400> SEQUENCE: 12

000

<210> SEQ ID NO 13
<211> LENGTH: 13
<212> TYPE: RNA
<213> ORGANISM: Artificial Sequence
<220> FEATURE:
<223> OTHER INFORMATION: Synthetic oligonucleotide

<400> SEQUENCE: 13

```
gccgccacca ugg                                                        13
```

<210> SEQ ID NO 14
<211> LENGTH: 22
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n = c or u
<220> FEATURE:
<221> NAME/KEY: misc_feature
<222> LOCATION: (5)..(9)
<223> OTHER INFORMATION: n = a, c, u, or g, and may be present or absent

```
<220> FEATURE:
<221> NAME/KEY: misc_feature
<222> LOCATION: (13)..(13)
<223> OTHER INFORMATION: n = a or u
<220> FEATURE:
<221> NAME/KEY: misc_feature
<222> LOCATION: (14)..(17)
<223> OTHER INFORMATION: n = c or u, and may be present or absent
<220> FEATURE:
<221> NAME/KEY: misc_feature
<222> LOCATION: (20)..(20)
<223> OTHER INFORMATION: n = c or u

<400> SEQUENCE: 14
nccannnnnc ccnnnnnucn cc                                            22
```

PHARMACEUTICAL COMPOSITION CONTAINING A STABILISED MRNA OPTIMISED FOR TRANSLATION IN ITS CODING REGIONS

CROSS REFERENCE TO RELATED APPLICATIONS

The present application is a continuation of U.S. application Ser. No. 14/487,425, filed Sep. 16, 2014, which is a divisional of U.S. application Ser. No. 10/729,830, filed Dec. 5, 2003, which is a Continuation-In-Part of PCT Application No. PCT/EP02/06180 filed Jun. 5, 2002, which in turn, claims priority from German Application No. DE 101 27 283.9, filed Jun. 5, 2001. Applicants claim the benefits of 35 U.S.C. § 120 as to the U.S. applications and PCT application and priority under 35 U.S.C. § 119 as to the said German application, and the disclosures of all of the above-referenced applications are incorporated herein in their entireties.

REFERENCE TO COMPUTER PROGRAM LISTING SUBMITTED AS AN ASCII FILE

This application includes a computer program listing, which is found in the Computer Program Listing Appendix filed electronically with the U.S. Patent and Trademark Office on Jan. 25, 2016. The Computer Program Listing Appendix, which is hereby incorporated by reference in its entirety, is contained in the file named "CRVCP0003USComputerListing.txt" that was created on Jan. 25, 2016, and has a file size of 55 KB (as measured in Microsoft Windows®).

INCORPORATION OF SEQUENCE LISTING

The sequence listing that is contained in the file named "CRVCP0003USC10_ST25_20)_MAYB2019.txt", which is 18 KB (as measured in Microsoft Windows®) and was created on May 20 2019, is filed herewith by electronic submission and is incorporated by reference herein.

BACKGROUND OF THE INVENTION

1. Field of the Invention

The present invention relates to a pharmaceutical composition containing an mRNA that is stabilised by sequence modifications in the translated region and is optimised for translation. The pharmaceutical composition according to the invention is suitable in particular as an inoculating agent and also as a therapeutic agent for tissue regeneration. Furthermore, a process for determining sequence modifications that stabilise mRNA and optimise mRNA translation is disclosed.

2. Description of the Prior Art

Gene therapy and genetic vaccination are tools of molecular medicine whose use in the treatment and prevention of diseases has considerable potential. Both of these approaches are based on the incorporation of nucleic acids into a patient's cells or tissue as well as on the subsequent processing of the information encoded by the incorporated nucleic acids, i.e. the expression of the desired polypeptides.

Conventional procedures involved in previous applications of gene therapy and genetic vaccination involved the use of DNA in order to incorporate the required genetic information into a cell. In this connection various processes for the incorporation of DNA into cells have been developed, such as for example calcium phosphate transfection, polyprene transfection, protoplast fusion, electroporation, microinjection and lipofection, in which connection lipofection in particular has proved to be a suitable process.

A further process that has been suggested in particular for the case of genetic vaccination involves the use of DNA viruses as DNA vehicles. Because such viruses are infectious, a very high transfection rate can be achieved when using DNA viruses as vehicles. The viruses used are genetically altered so that no functional infectious particles are formed in the transfected cell. Despite this precautionary measure, however, the risk of uncontrolled propagation of the introduced therapeutic gene as well as viral genes remains due to the possibility of recombination events.

Normally DNA incorporated into a cell is integrated to a certain extent into the genome of the transfected cell. On the one hand this phenomenon can exert a desirable effect, since in this way a long-lasting action of the introduced DNA can be achieved. On the other hand the integration into the genome brings with it a significant risk for gene therapy. Such integration events may, for example, involve an insertion of the incorporated DNA into an intact gene, which produces a mutation that interferes with or completely ablates the function of the endogenous gene. As a result of such integration events, enzyme systems that are important for cellular viability may be switched off. Alternatively, there is also the risk of inducing transformation of the transfected cell if the integration site occurs in a gene that is critical for regulating cell growth. Accordingly, when using DNA viruses as therapeutic agents and vaccines, a carcinogenic risk cannot be excluded. In this connection it should also be borne in mind that, in order to achieve effective expression of the genes incorporated into the cell, the corresponding DNA vehicles comprise a strong promoter, for example the viral CMV promoter. The integration of such promoters into the genome of the treated cell may, however, lead to undesirable changes in the regulation of the gene expression in the cell.

A further disadvantage of the use of DNA as a therapeutic agent or vaccine is the induction of pathogenic anti-DNA antibodies in the patient, resulting in a potentially fatal immune response.

In contrast to DNA, the use of RNA as a therapeutic agent or vaccine is regarded as significantly safer. In particular, use of RNA is not associated with a risk of stable integration into the genome of the transfected cell. In addition, no viral sequences such as promoters are necessary for effective transcription of RNA. Beyond this, RNA is degraded rapidly in vivo. Indeed, the relatively short half-life of RNA in circulating blood, as compared to that of DNA, reduces the risks associated with developing pathogenic anti-RNA antibodies. Indeed, anti-RNA antibodies have not been detected to date. For these reasons RNA may be regarded as the molecule of choice for molecular medicine therapeutic applications.

However, some basic problems still have to be solved before medical applications based on RNA expression systems can be widely employed. One of the problems in the use of RNA is the reliable, cell-specific and tissue-specific efficient transfer of the nucleic acid. Since RNA is normally found to be very unstable in solution, up to now RNA could not be used or used only very inefficiently as a therapeutic agent or inoculating agent in the conventional applications designed for DNA use.

Enzymes that break down RNA, so-called RNases (ribonucleases), are responsible in part for the instability. Even minute contamination by ribonucleases is sufficient to degrade down RNA completely in solution. Moreover, the natural decomposition of mRNA in the cytoplasm of cells is exquisitely regulated. Several mechanisms are known which contribute to this regulation. The terminal structure of a functional mRNA, for example, is of decisive importance. The so-called "cap structure" (a modified guanosine nucleotide) is located at the 5' end and a sequence of up to 200 adenosine nucleotides (the so-called poly-A tail) is located at the 3' end. The RNA is recognised as mRNA by virtue of these structures and these structures contribute to the regulatory machinery controlling mRNA degradation. In addition there are further mechanisms that stabilise or destabilise RNA. Many of these mechanisms are still unknown, although often an interaction between the RNA and proteins appears to be important in this regard. For example, an mRNA surveillance system has been described (Hellerin and Parker, Annu. Rev. Genet. 1999, 33: 229 to 260), in which incomplete or nonsense mRNA is recognised by specific feedback protein interactions in the cytosol and is made accessible to decomposition. Exonucleases appear to contribute in large measure to this process.

Certain measures have been proposed in the prior art to improve the stability of RNA and thereby enable its use as a therapeutic agent or RNA vaccine.

In EP-A-1083232 a process for the incorporation of RNA, in particular mRNA, into cells and organisms has been proposed in order to solve the aforementioned problem of the instability of RNA ex vivo. As described therein, the RNA is present in the form of a complex with a cationic peptide or protein.

WO 99/14346 describes further processes for stabilising mRNA. In particular, modifications of the mRNA are proposed that stabilise the mRNA species against decomposition by RNases. Such modifications may involve stabilisation by sequence modifications, in particular reduction of the C content and/or U content by base elimination or base substitution. Alternatively, chemical modifications may be used, in particular the use of nucleotide analogues, as well as 5' and 3' blocking groups, an increased length of the poly-A tail as well as the complexing of the mRNA with stabilising agents, and combinations of the aforementioned measures.

In U.S. Pat. Nos. 5,580,859 and 6,214,804 mRNA vaccines and mRNA therapeutic agents are disclosed inter alia within the scope of "transient gene therapy" (TGT). Various measures are described therein for enhancing the translation efficiency and mRNA stability that relate in particular to the composition of the non-translated sequence regions.

Bieler and Wagner (in: Schleef (Ed.), Plasmids for Therapy and Vaccination, Chapter 9, pp. 147 to 168, Wiley-VCH, Weinheim, 2001) report on the use of synthetic genes in combination with gene therapy methods employing DNA vaccines and lentiviral vectors. The construction of a synthetic gag-gene derived from HIV-1 is described, in which the codons have been modified with respect to the wild type sequence (alternative codon usage) in such a way as to correspond to frequently used codons found in highly expressed mammalian genes. In this way, in particular, the A/T content compared to the wild type sequence was reduced. Moreover, the authors found an increased rate of expression of the synthetic gag gene in transfected cells. Furthermore, increased antibody formation against the gag protein was observed in mice immunised with the synthetic DNA construct. An increase in cytokine release in vitro from transfected spleen cells of such mice was also observed. Finally, an induction of a cytotoxic immune response in mice immunised with the gag expression plasmid was also found. The authors of this article attribute the improved properties of their DNA vaccine to a change in the nucleocytoplasmic transport of the mRNA expressed by the DNA vaccine, which was due to the optimised codon usage. The authors maintain that the effect of the altered codon usage on the translation efficiency was only slight.

SUMMARY OF THE INVENTION

The object of the present invention is to provide a new system for gene therapy and genetic vaccination that overcomes the disadvantages associated with the properties of DNA therapeutic agents and DNA vaccines and increases the effectiveness of therapeutic agents based on RNA species.

This object is achieved by the embodiments of the present invention characterised in the claims.

In particular, a modified mRNA, as well as a pharmaceutical composition comprising at least one modified mRNA of the present invention and a pharmaceutically compatible carrier and/or vehicle are provided. The modified mRNA encodes at least one biologically active or antigenic peptide or polypeptide, wherein the sequence of the mRNA comprises at least one modification as set forth herein below as compared to the wild type mRNA. Such modifications may be located in the region coding for the at least one peptide or polypeptide, or in untranslated regions.

In one aspect, the G/C content of the region of the modified mRNA coding for the peptide or polypeptide is increased relative to that of the G/C content of the coding region of the wild type mRNA coding for the peptide or polypeptide. The encoded amino acid sequence, however, remains unchanged compared to the wild type. (i.e. silent with respect to the encoded amino acid sequence).

This modification is based on the fact that, for efficient translation of an mRNA, the sequence of the region of the mRNA to be translated is essential. In this connection the composition and the sequence of the various nucleotides play an important role. In particular sequences with an increased G (guanosine)/C(cytosine) content are more stable than sequences with an increased A(adenosine)/U (uracil) content. In accordance with the invention, the codons are varied compared to the wild type mRNA, while maintaining the translated amino acid sequence, so that they contain increased amounts of G/C nucleotides. Since several different codons can encode the same amino acid, due to degeneracy of the genetic code, the codons most favourable for the stability of the modified mRNA can be determined and incorporated (alternative codon usage).

Depending on the amino acid encoded by the modified mRNA, various possibilities for modifying the mRNA sequence compared to the wild type sequence are feasible. In the case of amino acids that are encoded by codons that contain exclusively G or C nucleotides, no modification of the codon is necessary. Thus, the codons for Pro (CCC or CCG), Arg (CGC or CGG), Ala (GCC or GCG) and Gly (GGC or GGG) do not require any alteration since no A or U is present.

In the following cases the codons that contain A and/or U nucleotides are altered by substituting other codons that code for the same amino acids, but do not contain A and/or U. Examples include: the codons for Pro, which may be changed from CCU or CCA to CCC or CCG; the codons for Arg, which may be changed from CGU or CGA or AGA or AGG to CGC or CGG; the codons for Ala, which may be changed from GCU or GCA to GCC or GCG; the codons for Gly, which may be changed from GGU or GGA to GGC or GGG.

In other cases, wherein A and/or U nucleotides may not be eliminated from the codons, it is however possible to reduce the A and U content by using codons that contain fewer A and/or U nucleotides. For example: the codons for Phe, which may be changed from UUU to UUC; the codons for Leu, which may be changed from UUA, CUU or CUA to CUC or CUG; the codons for Ser, which may be changed from UCU or UCA or AGU to UCC, UCG or AGC; the codon for Tyr, which may be changed from UAU to UAC; the stop codon UAA, which may be changed to UAG or UGA; the codon for Cys, which may be changed from UGU to UGC; the codon for His, which may be changed from CAU to CAC; the codon for Gln, which may be changed from CAA to CAG; the codons for Ile, which may be changed from AUU or AUA to AUC; the codons for Thr, which may be changed from ACU or ACA to ACC or ACG; the codon for Asn, which may be changed from AAU to AAC; the codon for Lys, which may be changed from AAA to AAG; the codons for Val, which may be changed from GUU or GUA to GUC or GUG; the codon for Asp, which may be changed from GAU to GAC; the codon for Glu, which may be changed from GAA to GAG.

In the case of the codons for Met (AUG) and Trp (UGG) there is however no possibility of modifying the sequence.

The substitutions listed above may be used individually and in all possible combinations in order to increase the G/C content of a modified mRNA compared to the original sequence. Thus, for example all codons for Thr occurring in the original (wild type) sequence can be altered to ACC (or ACG). Preferably, however, combinations of the substitution possibilities given above are employed, for example: substitution of all codons coding in the original sequence for Thr to ACC (or ACG) and substitution of all codons coding for Ser to UCC (or UCG or AGC); substitution of all codons coding in the original sequence for Ile to AUC and substitution of all codons coding for Lys to AAG and substitution of all codons coding originally for Tyr to UAC; substitution of all codons coding in the original sequence for Val to GUC (or GUG) and substitution of all codons coding for Glu to GAG and substitution of all codons coding for Ala to GCC (or GCG) and substitution of all codons coding for Arg to CGC (or CGG); substitution of all codons coding in the original sequence for Val to GUC (or GUG) and substitution of all codons coding for Glu to GAG and substitution of all codons coding for Ala to GCC (or GCG) and substitution of all codons coding for Gly to GGC (or GGG) and substitution of all codons coding for Asn to AAC; substitution of all codons coding in the original sequence for Val to GUC (or GUG) and substitution of all codons coding for Phe to UUC and substitution of all codons coding for Cys to UGC and substitution of all codons coding for Leu to CUG (or CUC) and substitution of all codons coding for Gln to CAG and substitution of all codons encoding Pro to CCC (or CCG); etc.

Preferably the G/C content of the region of the modified mRNA coding for the peptide or polypeptide is increased by at least 7%, more preferably by at least 15%, and particularly preferably by at least 20% compared to the G/C content of the coded region of the wild type mRNA encoding for the polypeptide.

In this connection it is particularly preferred to maximise the G/C content of the modified mRNA as compared to that of the wild type sequence. For some applications, it may be particularly advantageous to maximise the G/C content of the modified mRNA in the region encoding the at least one peptide or polypeptide.

In accordance with the invention, a further modification of the mRNA comprised in the pharmaceutical composition of the present invention is based on an understanding that the translational efficiency is also affected by the relative abundance of different tRNAs in various cells. A high frequency of so-called "rare" codons in an RNA sequence, which are recognized by relatively rare tRNAs, tends to decrease the translational efficiency of the corresponding mRNA, whereas a high frequency of codons recognized by relatively abundant tRNAs tends to enhance the translational efficiency of a corresponding mRNA.

Thus, according to the invention, the modified mRNA (which is contained in the pharmaceutical composition) comprises a region coding for the peptide or polypeptide which is changed compared to the corresponding region of the wild type mRNA so as to replace at least one codon of the wild type sequence that is recognized by a rare cellular tRNA with a codon recognized by an abundant cellular tRNA, wherein the abundant and rare cellular tRNAs recognize the same amino acid. In other words, the substituted codon in the modified mRNA, which is recognized by a relatively frequent tRNA, encodes the same amino acid as the wild type (unmodified) codon.

Through such modifications, the RNA sequences are modified so that codons are inserted/substituted that are recognized by abundantly expressed cellular tRNAs. Modifications directed to altering codon usage in a nucleic acid sequence to optimise expression levels of polypeptides encoded therefrom are generally referred to in the art as "codon optimisation".

Those tRNAs which are abundant or rare in a particular cell are known to a person skilled in the art; see for example Akashi, Curr. Opin. Genet. Dev. 2001, 11(6): 660-666. Each organism has a preferred choice of nucleotide or codon usage to encode any particular amino acid. Different species vary in their codon preferences for translating mRNA into protein. The codon preferences of a particular species in which a modified mRNA of the present invention is to be expressed will, therefore, at least in part dictate the parameters of codon optimisation for a nucleic acid sequence.

By means of this modification, according to the invention all codons of the wild type sequence that are recognized by a relatively rare tRNA in a cell may in each case be replaced by a codon that is recognized by a relatively abundant tRNA. As described herein, however, the coding sequence of the peptide or polypeptide is preserved. That is, a relatively abundant tRNA species, which replaces a relatively rare tRNA species in a modified mRNA of the invention, recognizes an amino acid identical to that recognized by the rare tRNA species.

According to the invention, it is particularly preferred to couple the sequential increase in the G/C fraction of a modified mRNA (particularly, for example, a maximally modified G/C content), with an increase in the number of codons recognized by abundant tRNAs, wherein the amino acid sequence of the peptide or polypeptide (one or more) encoded by the mRNA remains unaltered. This preferred embodiment provides a particularly preferred mRNA species, possessing properties of efficient translation and improved stability. Such preferred mRNA species are well suited, for example, for the pharmaceutical compositions of the present invention.

Sequences of eukaryotic mRNAs frequently include destabilising sequence elements (DSE) to which signal proteins can bind and thereby regulate the enzymatic degradation of the mRNA in vivo. Accordingly, for the further stabilisation of a modified mRNA of the invention, which may be a component of a pharmaceutical composition of the invention, one or more changes may be made in the wild type mRNA sequence encoding the at least one peptide or polypeptide, so as to reduce the number of destabilising sequence elements present. In accordance with the invention, DSEs located anywhere in an mRNA, including the coding region and in the non-translated regions (3' and/or 5' UTR), may be mutated or changed to generate a modified mRNA having improved properties.

Such destabilising sequences are for example AU-rich sequences ("AURES") that occur in 3'-UTR regions of a number of unstable mRNAs (Caput et al., Proc. Natl. Acad. Sci. USA 1986, 83: 1670-1674). The RNA molecules contained in the pharmaceutical composition according to the invention are therefore preferably altered as compared to the wild type mRNA so as to reduce the number of or eliminate these destabilising sequences. Such an approach also applies to those sequence motifs recognised by potential endonucleases. Such sequences include, for example, GAACAAG, which is found in the 3'UTR of the gene encoding the transferring receptor (Binder et al., EMBO J. 1994, 13: 1969-1980). Sequence motifs recognized by endonucleases are also preferably reduced in number or eliminated in the modified mRNA of the pharmaceutical composition according to the invention.

Various methods are known to the person skilled in the art that are suitable for the substitution of codons in the modified mRNA according to the invention. In the case of relatively short coding regions (that code for biologically active or antigenic peptides), the whole mRNA may, for example, be chemically synthesised using standard techniques.

Preferably, however, base substitutions are introduced using a DNA matrix for the production of modified mRNA with the aid of techniques routinely employed in targeted mutagenesis; see Maniatis et al., Molecular Cloning: A Laboratory Manual, Cold Spring Harbor Laboratory Press, $3^{rd}$ Edition, Cold Spring Harbor, N. Y., 2001.

In this method, a corresponding DNA molecule is therefore transcribed in vitro for the production of the mRNA. This DNA matrix has a suitable promoter, for example a T7 or SP6 promoter, for in vitro transcription, followed by the desired nucleotide sequence for the mRNA to be produced and a termination signal for the in vitro transcription. According to the invention the DNA molecule that forms the matrix of the RNA construct to be produced is prepared as part of a plasmid replicable in bacteria, wherein the plasmid is replicated or amplified during the course of bacterial replication and subsequently isolated by standard techniques. Plasmids suitable for use in the present invention include, but are not limited to pT7 Ts (GenBank Accession No. U26404; Lai et al., Development 1995, 121: 2349-2360), the pGEM® series, for example pGEM®-1 (GenBank Accession No. X65300; from Promega) and pSP64 (GenBank-Accession No. X65327); see also Mezei and Storts, Purification of PCR Products, in: Griffin and Griffin (Eds.), PCR Technology: Current Innovation, CRC Press, Boca Raton, Fla., 2001.

Thus, by using short synthetic DNA oligonucleotides that comprise short single-strand transitions at the corresponding cleavage sites, or by means of genes produced by chemical synthesis, the desired nucleotide sequence can be cloned into a suitable plasmid by molecular biology methods known to the person skilled in the art (see Maniatis et al., above). The DNA molecule is then excised from the plasmid, in which it may be present as a single copy or multiple copies, by digestion with restriction endonucleases.

The modified mRNA that is contained in the pharmaceutical composition according to the invention may furthermore have a 5' cap structure (a modified guanosine nucleotide). Examples of suitable cap structures include, but are not limited to m7G(5')ppp (5'(A,G(5')ppp(5')A and G(5')ppp (5')G.

According to a further preferred embodiment of the present invention the modified mRNA comprises a poly-A tail of at least 50 nucleotides, preferably at least 70 nucleotides, more preferably at least 100 nucleotides and particularly preferably at least 200 nucleotides.

For efficient translation of the mRNA an productive binding of the ribosomes to the ribosome binding site [Kozak sequence: GCCGCCACCAUGG (SEQ ID NO: 13), the AUG forms the start codon] is generally required. In this regard it has been established that an increased A/U content around this site facilitates more efficient ribosome binding to the mRNA.

In addition, it is possible to introduce one or more so-called IRES ("internal ribosomal entry site") into the modified mRNA. An IRES may act as the sole ribosome binding site, or may serve as one of the ribosome binding sites of an mRNA. An mRNA comprising more than one functional ribosome binding site may encode several peptides or polypeptides that are translated independently by the ribosomes ("multicistronic mRNA"). Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

According to a further preferred embodiment of the present invention the modified mRNA comprises in the 5' non-translated and/or 3' non-translated regions stabilisation sequences that are capable of increasing the half-life of the mRNA in the cytosol.

These stabilization sequences may exhibit 100% sequence homology with naturally occurring sequences that are present in viruses, bacteria and eukaryotic cells, or may be derived from such naturally occurring sequences (i.e., may comprise, e.g., mutations, substitutions, or deletions in these sequences). Stabilizing sequences that may be used in the present invention include, by way of non-limiting example, the untranslated sequences (UTR) of the β-globin gene of *Homo sapiens* or *Xenopus laevis*. Another example of a stabilization sequence has the general formula (C/U) CCAN$_x$CCC(U/A)Py$_x$UC(C/U)CC (SEQ ID NO: 14), which is contained in the 3'UTR of the very stable mRNAs that encode α-globin, α-(I)-collagen, 15-lipoxygenase, or tyrosine hydroxylase (C. F. Holcik et al., Proc. Natl. Acad. Sci. USA 1997, 94: 2410-2414). Obviously such stabilization sequences may be used individually or in combination, as well as in combination with other stabilization sequences known to a person skilled in the art.

For the further stabilisation of the modified mRNA it is preferred that the modified mRNA comprises at least one analogue of a naturally occurring nucleotide. This approach is based on the understanding that RNA-decomposing enzymes present in a cell preferentially recognise RNA comprising naturally occurring nucleotides as a substrate. The insertion of nucleotide analogues into an RNA molecule, therefore, retards decomposition of the RNA molecule so modified, whereas the effect of such analogs on translational efficiency, particularly when inserted into the coding region of the mRNA, may result in either an increase or decrease in translation of the modified RNA molecule.

The following is a non-limiting list of nucleotide analogues that can be used in accordance with the invention: phosphorus amidates, phosphorus thioates, peptide nucleotides, methylphosphonates, 7-deazaguanosine, 5-methylcytosine and inosine. The preparation of such analogues is known to the person skilled in the art, for example from U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642. According to the invention such analogues may be present in non-translated and/or translated regions of the modified mRNA.

Furthermore the effective transfer of the modified mRNA into the cells to be treated or into the organism to be treated may be improved if the modified mRNA is associated with a cationic peptide or protein, or is bound thereto. In particular in this connection the use of protamine as polycationic, nucleic acid-binding protein is particularly effective. It is also possible to use other cationic peptides or proteins such as poly-L-lysine or histones. Procedures for stabilising mRNA are described in EP-A-1083232, whose relevant disclosure is incorporated herein in its entirety.

For gene therapy applications, for example, wherein a pharmaceutical composition of the invention is used, the modified mRNA therein codes for at least one biologically active peptide or polypeptide that is not formed or is only insufficiently or defectively formed in the patient to be treated. Administration of a modified mRNA encoding the at least one biologically active peptide or polypeptide or a composition thereof to such a patient, therefore, at least partially restores the expression and/or activity of the at least one biologically active peptide or polypeptide in the patient and thereby complements the patient's genetic defect. The direct introduction of a normal, functional gene into a living animal has been studied as a means for replacing defective genetic information. In such studies, nucleic acid sequences are introduced directly into cells of a living animal. The following references pertain to methods for the direct introduction of nucleic acid sequences into a living animal: Nabel et al., (1990) Science 249:1285-1288; Wolfe et al., (1990) Science 247:1465-1468; Acsadi et al. (1991) Nature 352: 815-818; Wolfe et al. (1991) BioTechniques 11(4):474-485; and Feigner and Rhodes, (1991) Nature 349:351-352, which are incorporated herein by reference.

Accordingly, examples of polypeptides coded by a modified mRNA of the invention include, without limitation, dystrophin, the chloride channel, which is defectively altered in cystic fibrosis; enzymes that are lacking or defective in metabolic disorders such as phenylketonuria, galactosaemia, homocystinuria, adenosine deaminase deficiency, etc.; enzymes that are involved in the synthesis of neurotransmitters such as dopamine, norepinephrine and GABA, in particular tyrosine hydroxylase and DOPA decarboxylase, and α-1-antitrypsin, etc. Pharmaceutical compositions of the invention may also be used to effect expression of cell surface receptors and/or binding partners of cell surface receptors if the modified mRNA contained therein encodes for such biologically active proteins or peptides. Examples of such proteins that act in an extracellular manner or that bind to cell surface receptors include for example tissue plasminogen activator (TPA), growth hormones, insulin, interferons, granulocyte-macrophage colony stimulating factor (GM-CFS), and erythropoietin (EPO), etc.

By choosing suitable growth factors, the pharmaceutical composition of the present invention may, for example, be used for tissue regeneration. In this way diseases that are characterised by tissue degeneration, for example neurodegenerative diseases such as Alzheimer's disease, Parkinson's disease, etc. and other degenerative conditions, such as arthrosis, can be treated. In these cases the modified mRNA, in particular that contained in the pharmaceutical composition of the present invention, preferably encodes, without limitation, a TGF-β family member, EGF, FGF, PDGF, BMP, GDNF, BDNF, GDF and neurotrophic factors such as NGF, neutrophines, etc.

A further area of application of the present invention is vaccination, i.e. the use of a modified mRNA for inoculation or the use of a pharmaceutical composition comprising a modified mRNA as an inoculating agent, or the use of a modified mRNA in the preparation of the pharmaceutical composition for inoculation purposes. Vaccination is based on introducing an antigen into an organism or subject, in particular into a cell of the organism or subject. In the context of the present invention, the genetic information encoding the antigen is introduced into the organism or subject in the form of a modified mRNA encoding the antigen. The modified mRNA contained in the pharmaceutical composition is translated into the antigen, i.e. the polypeptide or antigenic peptide coded by the modified mRNA is expressed, and an immune response directed against the polypeptide or antigenic peptide is stimulated. For vaccination against a pathogenic organism, e.g., a virus, a bacterium, or a protozoan, a surface antigen of such an organism may be used as an antigen against which an immune response is elicited. In the context of the present invention, a pharmaceutical composition comprising a modified mRNA encoding such a surface antigen may be used as a vaccine. In applications wherein a genetic vaccine is used for treating cancer, the immune response is directed against tumour antigens by generating a modified mRNA encoding a tumour antigen(s), in particular a protein which is expressed exclusively on cancer cells. Such a modified mRNA encoding a tumour antigen may be used alone or as a component of a pharmaceutical composition according to the invention, wherein administration of either the modified mRNA or a composition thereof results in expression of the cancer antigen(s) in the organism. An immune response to such a vaccine would, therefore, confer to the vaccinated subject a degree of protective immunity against cancers associated with the immunizing cancer antigen. Alternatively, such measures could be used to vaccinate a cancer patient with a modified mRNA encoding a tumour antigen(s) expressed on the patient's cancer cells so as to stimulate the cancer patient's immune response to attack any cancer cells expressing the encoded antigen.

In its use as a vaccine the pharmaceutical composition according to the invention is suitable in particular for the treatment of cancers (in which the modified mRNA codes for a tumour-specific surface antigen (TSSA), for example for treating malignant melanoma, colon carcinoma, lymphomas, sarcomas, small-cell lung carcinomas, blastomas, etc. A non-limiting list of specific examples of tumour antigens include, inter alia, 707-AP, AFP, ART-4, BAGE, β-catenin/m, Bcr-abl, CAMEL, CAP-1, CASP-8, CDC27/m, CDK4/m, CEA, CT, Cyp-B, DAM, ELF2M, ETV6-AML1, G250, GAGE, GnT-V, Gp100, HAGE, HER-2/neu, HLA-A*0201-R170I, HPV-E7, HSP70-2M, HAST-2, hTERT (or hTRT), iCE, KIAA0205, LAGE, LDLR/FUT, MAGE, MART-1/melan-A, MC1R, myosin/m, MUC1, MUM-1, -2, -3, NA88-A, NY-ESO-1, p190 minor bcr-abl, Pml/RARα, PRAME, PSA, PSM, RAGE, RU1 or RU2, SAGE, SART-1 or SART-3, TEL/AML1, TPI/m, TRP-1, TRP-2, TRP-2/INT2 and WT1. In addition to the above application, the pharmaceutical composition of the invention may be used to treat infectious diseases, for example, viral infectious diseases such as AIDS (HIV), hepatitis A, B or C, herpes, herpes zoster (chicken pox), German measles (rubella virus), yellow fever, dengue fever etc. (flavi viruses), flu (influenza viruses), haemorrhagic infectious diseases (Marburg or Ebola viruses), bacterial infectious diseases such as Legionnaires' disease (*Legionella*), gastric ulcer (*Helicobacter*), cholera (*Vibrio*), *E. coli* infections, staphylococcal infections, *salmonella* infections or streptococcal infections, tetanus (*Clostridium tetani*), or protozoan infectious diseases (malaria, sleeping sickness, leishmaniasis, toxoplasmosis, i.e. infections caused by *plasmodium*, trypanosomes, *leishmania* and *toxoplasma*). Preferably also in the case of infectious diseases the corresponding surface antigens with the strongest antigenic potential are encoded by the modified mRNA. With the aforementioned genes of pathogenic vectors or organisms, in particular in the case of viral genes, this is typically a secreted form of a surface antigen. Moreover, according to the invention mRNAs preferably coding for polypeptides are employed, because polypeptides generally comprise multiple epitopes (polyepitopes). Polypeptides comprising polyepitopes include but are not limited to, surface antigens of pathogenic vectors or organisms, or of tumour cells, preferably secreted protein forms.

Moreover, the modified mRNA according to the invention may comprise in addition to the antigenic or therapeutically active peptide or polypeptide, at least one further functional region that encodes, for example, a cytokine that promotes the immune response (e.g., a monokine, lymphokine, interleukin or chemokine, such as IL-1, IL-2, IL-3, IL-4, IL-5, IL-6, IL-7, IL-8, IL-9, IL-10, IL-12, INF-α, INF-γ, GM-CFS, LT-α or growth factors such as hGH).

Furthermore, in order to increase immunogenicity, the pharmaceutical composition according to the invention may contain one or more adjuvants. The term "adjuvant" is understood in this context to denote any chemical or biological compound that promotes or augments a specific immune response. Various mechanisms may be involved in this connection, depending on the various types of adjuvants. For example, compounds that promote endocytosis of the modified mRNA contained in the pharmaceutical composition by dentritic cells (DC) form a first class of usable adjuvants. Other compounds that activate or accelerate maturation of DC (for example, lipopolysaccharides, TNF-α or CD40 ligand) comprise a second class of suitable adjuvants. In general, any agent which is recognized as a potential "danger signal" by the immune system (LPS, GP96, oligonucleotides with the CpG motif) or cytokines such as GM-CSF, may be used as an adjuvant. Co-administration of an adjuvant enhances an immune response generated against an antigen encoded by the modified mRNA. The aforementioned cytokines are particularly preferred in this aspect. Other known adjuvants include aluminium hydroxide, and Freund's adjuvant, as well as the aforementioned stabilising cationic peptides or polypeptides such as protamine. In addition, lipopeptides such as Pam3Cys are also particularly suitable for use as adjuvants in the pharmaceutical composition of the present invention; see Deres et al, Nature 1989, 342: 561-564.

The pharmaceutical composition according to the invention comprises, in addition to the modified mRNA, a pharmaceutically compatible carrier and/or a pharmaceutically compatible vehicle. Appropriate methods for achieving a suitable formulation and preparation of the pharmaceutical composition according to the invention are described in "Remington's Pharmaceutical Sciences" (Mack Pub. Co., Easton, Pa., 1980), which is herein incorporated by reference in its entirety. For parenteral administration suitable carriers include for example sterile water, sterile saline solutions, polyalkylene glycols, hydrogenated naphthalene and in particular biocompatible lactide polymers, lactide/glycolide copolymers or polyoxyethylene/polyoxypropylene copolymers. Compositions according to the invention may contain fillers or substances such as lactose, mannitol, substances for the covalent coupling of polymers such as for example polyethylene glycol to inhibitors according to the invention, complexing with metal ions or incorporation of materials in or on special preparations of polymer compound, such as for example polylactate, polyglycolic acid, hydrogel or on liposomes, microemulsions, microcells, unilamellar or multilamellar vesicles, erythrocyte fragments or spheroplasts. The respective modifications of the compositions are chosen depending on physical properties such as, for example, solubility, stability, bioavailability or degradability. Controlled or constant release of the active component according to the invention in the composition includes formulations based on lipophilic depot substances (for example fatty acids, waxes or oils). Coatings of substances or compositions according to the invention containing such substances, namely coatings with polymers (for example poloxamers or poloxamines), are also disclosed within the scope of the present invention. Moreover substances or compositions according to the invention may contain protective coatings, for example protease inhibitors or permeability enhancers. Preferred carriers are typically aqueous carrier materials, in which water for injection (WFI) or water buffered with phosphate, citrate or acetate, etc., is used, and the pH is typically adjusted to 5.0 to 8.0, preferably 6.0 to 7.0. The carrier or the vehicle will in addition preferably contain salt constituents, for example sodium chloride, potassium chloride or other components that for example make the solution isotonic. In addition the carrier or the vehicle may contain, besides the aforementioned constituents, additional components such as human serum albumin (HSA), polysorbate 80, sugars or amino acids.

The concentration of the modified mRNA in such formulations may therefore vary within a wide range from 1 μg to 100 mg/ml. The pharmaceutical composition according to the invention is preferably administered parenterally, for example intravenously, intraarterially, subcutaneously or intramuscularly to the patient. It is also possible to administer the pharmaceutical composition topically or orally.

The invention thus also provides a method for the treatment of the aforementioned medical conditions or an inoculation method for the prevention of the aforementioned conditions, which comprises the administration of the pharmaceutical composition according to the invention to a subject or patient, in particular a human patient.

A typical regimen for preventing, suppressing, or treating a pathology related to a viral, bacterial, or protozoan infection, may comprise administration of an effective amount of a vaccine composition as described herein, administered as a single treatment, or repeated as enhancing or booster dosages, over a period up to and including between one week and about 24 months, or any range or value therein.

According to the present invention, an "effective amount" of a vaccine composition is one that is sufficient to achieve a desired biological effect. It is understood that nature and manner of the administration and the effective dosage may be determined by a medical practitioner based on a number of variables including the age, sex, health, and weight of the recipient, the medical condition to be treated and its stage of progression, the kind of concurrent treatment, if any, frequency of treatment, and the nature of the desired outcome. The ranges of effective doses provided below are not intended to limit the invention, but are provided as representative preferred dose ranges. However, the most preferred dosage will be tailored to the individual subject, as is understood and determinable by one of skill in the art, without undue experimentation. See, e.g., Berkow et al., eds., The Merck Manual, 16th edition, Merck and Co., Rahway, N.J., 1992; Goodman et al., eds., Goodman and Gilman's The Pharmacological Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, Mass. (1985); and Katzung, ed. Basic and Clinical Pharmacology, Fifth Edition, Appleton and Lange, Norwalk, Conn. (1992), which references and references cited therein, are entirely incorporated herein by reference.

The present invention relates to the use of genetic material (e.g., nucleic acid sequences) as immunizing agents. In one aspect, the present invention relates to the introduction of exogenous or foreign modified DNA or RNA molecules into an individual's tissues or cells, wherein these molecules encode an exogenous protein capable of eliciting an immune response to the protein. The exogenous nucleic acid sequences may be introduced alone or in the context of an expression vector wherein the sequences are operably linked to promoters and/or enhancers capable of regulating the expression of the encoded proteins. The introduction of exogenous nucleic acid sequences may be performed in the presence of a cell stimulating agent capable of enhancing the uptake or incorporation of the nucleic acid sequences into a cell. Such exogenous nucleic acid sequences may be administered in a composition comprising a biologically compatible or pharmaceutically acceptable carrier. The exogenous nucleic acid sequences may be administered by a variety of means, as described herein, and well known in the art.

Such methods may be used to elicit immunity to a pathogen, absent the risk of infecting an individual with the pathogen. The present invention may be practiced using procedures known in the art, such as those described in PCT International Application Number PCT/US90/01515, wherein methods for immunizing an individual against pathogen infection by directly injecting polynucleotides into the individual's cells in a single step procedure are presented.

In one aspect, the present invention relates to methods for eliciting immune responses in an individual or subject which can protect the individual from pathogen infection. Accordingly, genetic material that encodes an immunogenic protein is introduced into a subject's cells either in vivo or ex vivo. The genetic material is expressed by these cells, thereby producing immunogenic target proteins capable of eliciting an immune response. The resulting immune response is broad based and involves activation of the humoral immune response and both arms of the cellular immune response.

This approach is useful for eliciting a broad range of immune responses against a target protein. Target proteins may be proteins specifically associated with pathogens or the individual's own "abnormal" or infected cells. Such an approach may be used advantageously to immunize a subject against pathogenic agents and organisms such that an immune response against a pathogen protein provides protective immunity against the pathogen. This approach is particularly useful for protecting an individual against infection by non-encapsulated intracellular pathogens, such as a virus, which produce proteins within the host cells. The immune response generated against such proteins is capable of eliminating infected cells with cytotoxic T cells (CTLs).

The immune response elicited by a target protein produced by vaccinated cells in a subject is a broad-based immune response which includes B cell and T cell responses, including CTL responses. It has been observed that target antigen produced within the cells of the host are processed intracellularly into small peptides, which are bound by Class I MHC molecules and presented in the context of Class I on the cell surface. The Class I MHC-target antigen complexes are capable of stimulating $CD8^+$ T cells, which are predominantly CTLs. Notably, genetic immunization according to the present invention is capable of eliciting CTL responses (killer cell responses).

The CTL response is crucial in protection against pathogens such as viruses and other intracellular pathogens which produce proteins within infected cells. Similarly, the CTL response can be utilized for the specific elimination of deleterious cell types, which may express aberrant cell surface proteins recognizable by Class I MHC molecules.

The genetic vaccines of the present invention may be administered to cells in conjunction with compounds that stimulate cell division and facilitate uptake of genetic constructs. This step provides an improved method of direct uptake of genetic material. Administration of cell stimulating compounds results in a more effective immune response against the target protein encoded by the genetic construct.

According to the present invention, modified DNA or mRNA that encodes a target protein is introduced into the cells of an individual where it is expressed, thus producing the target protein. The modified DNA or RNA may be operably linked to regulatory elements (e.g., a promoter) necessary for expression in the cells of the individual. Other elements known to skilled artisans may also be included in genetic constructs of the invention, depending on the application.

As used herein, the term "genetic construct" refers to the modified DNA or mRNA molecule that comprises a nucleotide sequence which encodes the target protein and which may include initiation and termination signals operably linked to regulatory elements including a promoter and polyadenylation signal (for modified DNA) capable of directing expression in the cells of the vaccinated individual. As used herein, the term "expressible form" refers to gene constructs which contain the necessary regulatory elements operably linked to a coding sequence of a target protein, such that when present in the cell of the individual, the coding sequence is expressed. As used herein, the term "genetic vaccine" refers to a pharmaceutical preparation that comprises a genetic construct.

The present invention provides genetic vaccines, which include genetic constructs comprising DNA or RNA which encode a target protein. As used herein, the term "target protein" refers to a protein capable of eliciting an immune response. The target protein is an immunogenic protein derived from the pathogen or undesirable cell-type, such as an infected or transformed cell. In accordance with the invention, target proteins may be pathogen-associated proteins or tumour-associated proteins. The immune response directed against the target protein protects the individual against the specific infection or disease with which the target protein is associated. For example, a genetic vaccine comprising a modified DNA or RNA molecule that encodes a pathogen-associated target protein is used to elicit an immune response that will protect the individual from infection by the pathogen.

DNA and RNA-based vaccines and methods of use are described in detail in several publications, including Leitner et al. (1999, Vaccines 18:765-777), Nagashunmugam et al. (1997, AIDS 11:1433-1444), and Fleeton et al. (2001, J Infect Dis 183:1395-1398) the entire contents of each of which is incorporated herein by reference.

In order to test expression, genetic constructs can be tested for expression levels in vitro using cells maintained in culture, which are of the same type as those to be vaccinated. For example, if the genetic vaccine is to be administered into human muscle cells, muscle cells grown in culture such as solid muscle tumor cells of rhabdomyosarcoma may be used as an in vitro model for measuring expression levels. One of ordinary skill in the art could readily identify a model in vitro system which may be used to measure expression levels of an encoded target protein.

In accordance with the invention, multiple inoculants can be delivered to different cells, cell types, or tissues in an individual. Such inoculants may comprise the same or different nucleic acid sequences of a pathogenic organism. This allows for the introduction of more than a single antigen target and maximizes the chances for developing immunity to the pathogen in a vaccinated subject.

According to the invention, the genetic vaccine may be introduced in vivo into cells of an individual to be immunized or ex vivo into cells of the individual which are re-implanted after incorporation of the genetic vaccine. Either route may be used to introduce genetic material into cells of an individual. As described herein above, preferred routes of administration include intramuscular, intraperitoneal, intradermal, and subcutaneous injection. Alternatively, the genetic vaccine may be introduced by various means into cells isolated from an individual. Such means include, for example, transfection, electroporation, and microprojectile bombardment. These methods and other protocols for introducing nucleic acid sequences into cells are known to and routinely practiced by skilled practitioners. After the genetic construct is incorporated into the cells, they are re-implanted into the individual. Prior to re-implantation, the expression levels of a target protein encoded by the genetic vaccine may be assessed. It is contemplated that otherwise non-immunogenic cells that have genetic constructs incorporated therein can be implanted into autologous or heterologous recipients.

The genetic vaccines according to the present invention comprise about 0.1 to about 1000 micrograms of nucleic acid sequences (i.e., DNA or RNA). In some preferred embodiments, the vaccines comprise about 1 to about 500 micrograms of nucleic acid sequences. In some preferred embodiments, the vaccines comprise about 25 to about 250 micrograms of nucleic acid sequences. Most preferably, the vaccines comprise about 100 micrograms nucleic acid sequences.

The genetic vaccines according to the present invention are formulated according to the mode of administration to be used. One having ordinary skill in the art can readily formulate a genetic vaccine that comprises a genetic construct. In cases where intramuscular injection is the chosen mode of administration, for example, an isotonic formulation is generally used. As described in detail herein above, additives for isotonicity can include sodium chloride, dextrose, mannitol, sorbitol and lactose. Isotonic solutions such as phosphate buffered saline are preferred. Stabilizers can include gelatin and albumin.

In some embodiments of the invention, the individual is administered a series of vaccinations to produce a comprehensive immune response. According to this method, at least two and preferably four injections are given over a period of time. The period of time between injections may include from 24 hours apart to two weeks or longer between injections, preferably one week apart. Alternatively, at least two and up to four separate injections may be administered simultaneously to different parts of the body.

While this disclosure generally discusses immunization or vaccination in the context of prophylactic methods of protection, the terms "immunizing" or "vaccinating" are meant to refer to both prophylactic and therapeutic methods. Thus, a method for immunizing or vaccinating includes both methods of protecting an individual from pathogen challenge, as well as methods for treating an individual suffering from pathogen infection. Accordingly, the present invention may be used as a vaccine for prophylactic protection or in a therapeutic manner; that is, as a reagent for immunotherapeutic methods and preparations.

The amount of a modified nucleic acid sequence generated using the methods of the invention which provides a therapeutically effective dose in the treatment of a patient with, for example, cancer or a pathogen-related disorder can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally directed to achieve a concentration of about 20-500 micrograms of polypeptide encoded by the modified nucleic acid per kilogram body weight. Suitable dosage ranges for intranasal administration are generally directed to achieve a concentration of about 0.01 pg to 1 mg of polypeptide encoded by the modified nucleic acid per kg body weight. Effective doses may be extrapolated from dose-response curves derived from in vitro or animal model test systems.

The compositions comprising the modified nucleic acid molecules of the invention can be administered for prophylactic and/or therapeutic treatments. In therapeutic applications, compositions are administered to a patient already suffering from a hyperproliferative disorder (such as, e.g., cancer) in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

Compositions comprising modified nucleic acid molecules of the invention can be administered alone, or in combination, and/or in conjunction with known therapeutic agents/compounds used for the treatment of a patient with a particular disorder. For the treatment of a patient with cancer, for example, a composition comprising at least one modified nucleic acid of the invention which encodes a tumour antigen, may be used in conjunction with one or more known cancer therapeutics, such as those described in the *Physicians' Desk Reference*, 50 *Edition* (2000) or in *Cancer: Principles & Practice of Oncology*, DeVita, Jr., Hellman, and Rosenberg (eds.) 2nd edition, Philadelphia, Pa.: J.B. Lippincott Co., 1985, wherein standard treatment protocols and dosage formulations are presented.

In addition a method is also provided for determining how to modify the sequence of an mRNA so as to generate a modified mRNA having altered properties, which may be used alone or in a pharmaceutical composition of the invention. In this connection, and in accordance with the invention, the modification of an RNA sequence is carried out with two different optimisation objectives: to maximize G/C content, and to maximize the frequency of codons that are recognized by abundantly expressed tRNAs. In the first step of the process a virtual translation of an arbitrary RNA (or DNA) sequence is carried out in order to generate the corresponding amino acid sequence. Starting from the amino acid sequence, a virtual reverse translation is performed that provides, based on degeneracy of the genetic code, all of the possible choices for the corresponding codons. Depending on the required optimisation or modification, corresponding selection lists and optimisation algorithms are used for choosing suitable codons. The algorithms are executed on a computer, normally with the aid of suitable software. In accordance with the present invention, a suitable software program comprises a source code of Appendix I. Thus, the optimised mRNA sequence is generated and can be output, for example, with the aid of a suitable display device and compared with the original (wild type) sequence. The same also applies with regard to the frequency of the individual nucleotides. The changes compared to the original nucleotide sequence are preferably emphasised. Furthermore, according to a preferred embodiment, naturally occurring stable sequences are incorporated therein to produce an RNA stabilised by the presence of natural sequence motifs. A secondary structural analysis may also be performed that can analyse, on the basis of structural calculations, stabilising and destabilising properties or regions of the RNA.

Also encompassed by the present invention are modified nucleic acid sequences generated using the above computer-based method. Exemplary modified nucleic acid sequences of the invention include SEQ ID NOs: 3-7, 10 and 11. The present invention also includes pharmaceutical compositions of modified nucleic acid sequences of the invention, including SEQ ID NOs: 3-7, 10 and 11.

BRIEF DESCRIPTION OF THE DRAWINGS

FIGS. 1A-G show wild type sequences and modified sequences for the influenza matrix protein.

FIG. 1A (SEQ ID NO: 1) shows the wild type gene and FIG. 1B (SEQ ID NO: 2) shows the amino acid sequence derived therefrom (1-letter code). FIG. 1C (SEQ ID NO: 3) shows a gene sequence coding for the influenza matrix protein, whose G/C content is increased as compared to that of the wild type sequence. FIG. 1D (SEQ ID NO: 4) shows the sequence of a gene that codes for a secreted form of the influenza matrix protein (including an N-terminal signal sequence), wherein the G/C content of the sequence is increased relative to that of the wild type sequence. FIG. 1E (SEQ ID NO: 5) shows an mRNA coding for the influenza matrix protein, wherein the mRNA comprises stabilising sequences not present in the corresponding wild type mRNA. FIG. 1F (SEQ ID NO: 6) shows an mRNA coding for the influenza matrix protein that in addition to stabilising sequences also contains an increased G/C content. FIG. 1G (SEQ ID NO: 7) likewise shows a modified mRNA that codes for a secreted form of the influenza matrix protein and comprises, as compared to the wild type, stabilising sequences and an elevated G/C content. In FIG. 1A and FIGS. 1C to 1G the start and stop codons are shown in bold type. Nucleotides that are changed relative to the wild type sequence of FIG. 1A are shown in capital letters in 1C to 1G.

FIGS. 2A-D show wild type sequences and modified sequences according to the invention that encode for the tumour antigen MAGE1.

FIG. 2A (SEQ ID NO: 8) shows the sequence of the wild type gene and FIG. 2B (SEQ ID NO: 9) shows the amino acid sequence derived therefrom (3-letter code). FIG. 2C (SEQ ID NO: 10) shows a modified mRNA coding for MAGE1, whose G/C content is increased as compared to the wild type. FIG. 2D (SEQ ID NO: 11) shows the sequence of a modified mRNA encoding MAGE1, in which the codon usage has been optimised as frequently as possible with respect to the tRNA present in the cell and to the coding sequence in question. Start and stop codons are shown in each case in bold type.

DETAILED DESCRIPTION OF THE PREFERRED EMBODIMENTS

The following examples describe the invention in more detail and in no way are to be construed as restricting the scope thereof.

Example 1

As an exemplary embodiment of the process for determining the sequence of a modified mRNA according to the invention, a computer program was established that modifies the nucleotide sequence of an arbitrary mRNA in such a way as to maximise the G/C content of the nucleic acid, and maximise the presence of codons recognized by abundant tRNAs present in a particular cell(s). The computer program is based on an understanding of the genetic code and exploits the degenerative nature of the genetic code. By this means a modified mRNA having desirable properties is obtained, wherein the amino acid sequence encoded by the modified mRNA is identical to that of the unmodified mRNA sequence. Alternatively, the invention may encompass alterations in either the G/C content or codon usage of an mRNA to produce a modified mRNA.

The source code in Visual Basic 6.0 (program development environment employed: Microsoft Visual Studio Enterprise 6.0 with Servicepack 3) is given in the Appendix I.

Example 2

An RNA construct with a sequence of the lac-Z gene from *E. coli* optimised with regard to stabilisation and translational efficiency was produced with the aid of the computer program of Example 1. A G/C content of 69% (compared to the wild type sequence of 51%; C. F. Kalnins et al., EMBO J. 1983, 2(4): 593-597) was achieved in this manner. Through the synthesis of overlapping oligonucleotides that comprise the modified sequence, the optimised sequence was produced according to methods known in the art. The terminal oligonucleotides have the following restriction cleavage sites: at the 5' end an EcoRV cleavage site, and at the 3' end a BglII cleavage site. The modified lacZ sequence was incorporated into the plasmid pT7 Ts (GenBank Accession No. U26404; C. F. Lai et al., see above) by digestion with EcoRV/BglII. pT7 Ts contains untranslated region sequences from the β-globin gene of *Xenopus laevis* at the 5' and 3' ends. The plasmid was cleaved with the aforementioned restriction enzymes to facilitate insertion of the modified lacZ sequence having compatible 5' and 3' termini.

The pT7 Ts-lac-Z construct was propagated in bacteria and purified by phenol-chloroform extraction. 2 µg of the construct were transcribed in vitro using methods known to a skilled artisan and the modified mRNA was produced.

Example 3

Figure 1A:
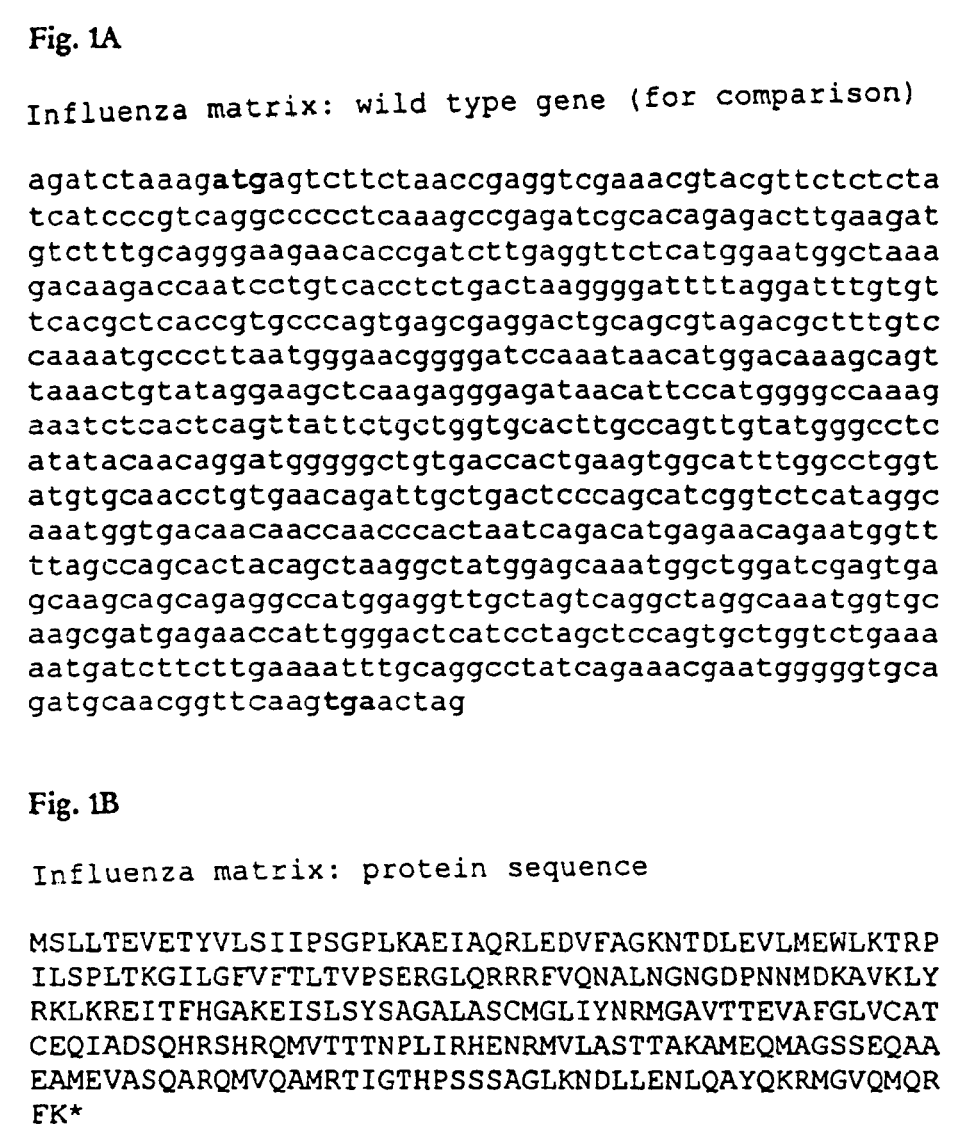

The gene for the influenza matrix protein (wild type sequence, see FIG. 1A; derived amino acid sequence, see FIG. 1B) was optimised with the aid of the computer program according to the invention of Example 1. The G/C-rich sequence variant shown in FIG. 1C (SEQ ID NO: 3) was thereby formed. A G/C-rich sequence coding for a secreted form of the influenza matrix protein, which includes an N-terminal signal sequence was also determined (see FIG. 1D; SEQ ID NO: 4). The secreted form of the influenza matrix protein has the advantage of increased immunogenicity as compared to that of the non-secreted form.

Corresponding mRNA molecules were designed starting from the optimised sequences. The mRNA for the influenza matrix protein, optimised with regard to G/C content and codon usage, was additionally provided with stabilising sequences in the 5' region and 3' region (the stabilisation sequences derive from the 5'-UTRs and 3'-UTRs of the β-globin-mRNA of *Xenopus laevis*; pT7 Ts-Vektor in C. F. Lai et al., see above). See also FIG. 1E; SEQ ID NO: 5, which includes only stabilising sequences and 1F; SEQ ID NO: 6, which includes both increased G/C content and stabilising sequences. The mRNA coding for the secreted form of the influenza matrix protein was likewise also sequence optimised in the translated region and provided with the aforementioned stabilising sequences (see FIG. 1G; SEQ ID NO: 7).

Example 4

The mRNA encoding the tumour antigen MAGE1 was modified with the aid of the computer program of Example 1. The sequence shown in FIG. 2C (SEQ ID NO: 10) was generated in this way, and has a 24% higher G/C content (351 G, 291 C) as compared to the wild type sequence (275 G, 244 G). In addition, by means of alternative codon usage, the wild type sequence was improved with regard to translational efficiency by substituting codons corresponding to tRNAs that are more abundant in a target cell (see FIG. 2D; SEQ ID NO: 11). The G/C content was likewise raised by 24% by the alternative codon usage.

What is claimed is:

1. A method of expressing a polypeptide in a subject comprising administering an effective amount of a pharmaceutical composition comprising a mRNA encoding the polypeptide to the subject, wherein the mRNA encoding polypeptide comprises at least one nucleotide of the mRNA that is substituted with an analog of a naturally occurring nucleotide, wherein the polypeptide encoded by the mRNA is a therapeutic polypeptide, which is not an infectious disease antigen or a tumor antigen, and wherein the mRNA that encodes the polypeptide comprises a coding sequence encoding the polypeptide with an increased G/C content of at least 7 percentage points relative to the coding sequence of an original RNA sequence encoding the polypeptide.

2. The method of claim 1, wherein the mRNA encoding the polypeptide comprises at least one nucleotide position replaced with a nucleotide analogue selected from the group consisting of phosphorus amidates, phosphorus thioates, peptide nucleotides, methylphosphonates, 7-deazaguanosine, 5-methylcytosine and inosine.

3. The method of claim 1, wherein the pharmaceutical composition is administered by injection.

4. The method of claim 1, wherein the pharmaceutical composition is administered intravenously, subcutaneously, intramuscularly, topically or orally.

5. The method of claim 1, wherein the mRNA encoding the polypeptide comprises a stabilizing 5' untranslated region (UTR) or 3' UTR.

6. The method of claim 1, wherein the mRNA comprises a 5' cap structure.

7. The method of claim 1, wherein the mRNA comprises a poly-A tail of at least 50 nucleotides.

8. The method of claim 1, wherein the therapeutic polypeptide comprises erythropoietin (EPO).

9. The method of claim 1, wherein the mRNA is dissolved in an aqueous carrier.

10. The method of claim 9, wherein the aqueous carrier is water for injection (WFI), a buffered solution or a salt solution.

11. The method of claim 10, wherein the salt solution comprises sodium chloride or potassium chloride solution.

12. The method of claim 1, wherein the pharmaceutical composition comprises a component selected from the group consisting of human serum albumin, a polycationic protein, polysorbate 80, a sugar and an amino acid.

13. The method of claim 12, wherein the pharmaceutical composition comprises a polycationic protein.

14. The method of claim 1, wherein the mRNA is provided in a liposome complex.

15. The method of claim 1, further comprising administering the pharmaceutical composition to the subject two or more times.

16. The method of claim 1, wherein the composition is administered by injection and wherein the mRNA is provided in a liposome complex.

17. The method of claim 1, wherein the subject has a disease.

18. The method of claim 1, wherein the mRNA that encodes the polypeptide comprises a coding sequence encoding the polypeptide with an increased G/C content of at least 15 percentage points relative to the coding sequence of an original RNA sequence encoding the polypeptide.

19. The method of claim 18, wherein the mRNA that encodes the polypeptide comprises a coding sequence encoding the polypeptide with an increased G/C content of at least 20 percentage points relative to the coding sequence of an original RNA sequence encoding the polypeptide.

* * * * *

UNITED STATES PATENT AND TRADEMARK OFFICE
CERTIFICATE OF CORRECTION

| | | |
|---|---|---|
| PATENT NO. | : 11,369,691 B2 | Page 1 of 1 |
| APPLICATION NO. | : 15/005986 | |
| DATED | : June 28, 2022 | |
| INVENTOR(S) | : Von Der Mülbe et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 852 days.

Signed and Sealed this
Eighteenth Day of February, 2025

Coke Morgan Stewart
*Acting Director of the United States Patent and Trademark Office*